(12) United States Patent
Swanick et al.

(10) Patent No.: US 9,427,423 B2
(45) Date of Patent: Aug. 30, 2016

(54) FATTY-ACID BASED PARTICLES

(75) Inventors: Thomas M. Swanick, Hillsborough, NH (US); Joseph Ferraro, Londonderry, NH (US); Lisa Rogers, Londonderry, NH (US); Paul Martakos, Pelham, NH (US)

(73) Assignee: ATRIUM MEDICAL CORPORATION, Merrimack, NH (US)

(*) Notice: Subject to any disclaimer, the term of this patent is extended or adjusted under 35 U.S.C. 154(b) by 157 days.

(21) Appl. No.: 12/401,243

(22) Filed: Mar. 10, 2009

(65) Prior Publication Data

US 2010/0233232 A1 Sep. 16, 2010

(51) Int. Cl.
| | |
|---|---|
| A61K 31/20 | (2006.01) |
| A61K 31/7028 | (2006.01) |
| A61K 38/13 | (2006.01) |
| A61K 9/10 | (2006.01) |
| A61K 31/4353 | (2006.01) |
| A61K 9/70 | (2006.01) |
| A61K 31/00 | (2006.01) |
| A61K 9/14 | (2006.01) |
| A61K 31/4545 | (2006.01) |
| A61K 31/496 | (2006.01) |

(52) U.S. Cl.
CPC .............. *A61K 31/20* (2013.01); *A61K 9/10* (2013.01); *A61K 9/145* (2013.01); *A61K 9/7007* (2013.01); *A61K 31/00* (2013.01); *A61K 31/4353* (2013.01); *A61K 31/4545* (2013.01); *A61K 31/496* (2013.01); *A61K 31/7028* (2013.01); *A61K 38/13* (2013.01)

(58) Field of Classification Search
None
See application file for complete search history.

(56) References Cited

U.S. PATENT DOCUMENTS

| | | | |
|---|---|---|---|
| 1,948,959 | A | 2/1934 | Croce |
| 2,368,306 | A | 1/1945 | Kiefer et al. |
| 2,403,458 | A | 7/1946 | Ransom |
| 2,735,814 | A | 2/1956 | Hodson et al. |
| 2,986,540 | A | 5/1961 | Posnansky |
| 3,464,413 | A | 9/1969 | Goldfarb et al. |
| 3,556,294 | A | 1/1971 | Walck et al. |
| 3,567,820 | A | 3/1971 | Sperti |
| 3,803,109 | A | 4/1974 | Nemoto et al. |
| 3,967,728 | A | 7/1976 | Gordon et al. |
| 4,308,120 | A | 12/1981 | Pennewiss et al. |
| 4,323,547 | A | 4/1982 | Knust et al. |
| 4,447,418 | A | 5/1984 | Maddoux |
| 4,557,925 | A | 12/1985 | Lindahl et al. |
| 4,664,114 | A | 5/1987 | Ghodstain |
| 4,813,210 | A | 3/1989 | Masuda et al. |
| 4,814,329 | A | 3/1989 | Harsanyi et al. |
| 4,847,301 | A | 7/1989 | Murray |
| 4,880,455 | A | 11/1989 | Blank |
| 4,883,667 | A | 11/1989 | Eckenhoff |
| 4,886,787 | A | 12/1989 | De Belder et al. |
| 4,894,231 | A | 1/1990 | Moreau et al. |
| 4,895,724 | A * | 1/1990 | Cardinal et al. .............. 424/418 |
| 4,911,707 | A | 3/1990 | Heiber et al. |
| 4,937,254 | A | 6/1990 | Sheffield et al. |
| 4,938,763 | A | 7/1990 | Dunn et al. |
| 4,941,308 | A | 7/1990 | Grabenkort et al. |
| 4,947,840 | A | 8/1990 | Yannas et al. |
| 4,952,419 | A | 8/1990 | De Leon |
| 4,968,302 | A | 11/1990 | Schluter et al. |
| 5,017,229 | A | 5/1991 | Burns et al. |
| 5,061,281 | A | 10/1991 | Mares et al. |
| 5,132,115 | A | 7/1992 | Wolter et al. |
| 5,147,374 | A | 9/1992 | Fernandez |
| 5,151,272 | A | 9/1992 | Engstrom et al. |
| 5,171,148 | A | 12/1992 | Wasserman et al. |
| 5,176,956 | A | 1/1993 | Jevne et al. |
| 5,179,174 | A | 1/1993 | Elton |
| 5,202,310 | A | 4/1993 | Levy et al. |
| 5,254,105 | A | 10/1993 | Haaga |
| 5,356,432 | A | 10/1994 | Rutkow et al. |
| 5,368,602 | A | 11/1994 | De La Torre |
| 5,371,109 | A | 12/1994 | Engstrom et al. |
| 5,380,328 | A | 1/1995 | Morgan |
| 5,387,658 | A | 2/1995 | Schroder et al. |
| 5,403,283 | A | 4/1995 | Luther |
| 5,411,951 | A | 5/1995 | Mitchell |
| 5,411,988 | A | 5/1995 | Bockow et al. |
| 5,447,940 | A | 9/1995 | Harvey et al. |

(Continued)

FOREIGN PATENT DOCUMENTS

| | | |
|---|---|---|
| EP | 0 471 566 | 2/1992 |
| EP | 0610731 | 8/1994 |

(Continued)

OTHER PUBLICATIONS

Final Office Action for U.S. Appl. No. 11/980,155, mailed Oct. 21, 2011.

(Continued)

*Primary Examiner* — Robert A Wax
*Assistant Examiner* — Caralynne Helm
(74) *Attorney, Agent, or Firm* — Wesley Scott Ashton

(57) ABSTRACT

The present invention is directed toward fatty acid-based particles, and methods of making such particles. The particles can be associated with an additional, therapeutic agent. Also provided herein is a method of forming fatty acid particles, comprising associating a cross-linked, fatty acid-derived biomaterial with a cryogenic liquid; and fragmenting the bio material/cryogenic liquid composition, such that fatty acid particles are formed. The particles can be used for a variety of therapeutic applications.

24 Claims, 7 Drawing Sheets

(56) References Cited

U.S. PATENT DOCUMENTS

| | | |
|---|---|---|
| 5,464,650 A | 11/1995 | Berg et al. |
| 5,480,653 A | 1/1996 | Aguadisch et al. |
| 5,509,899 A | 4/1996 | Fan et al. |
| 5,547,677 A | 8/1996 | Wright |
| 5,549,901 A | 8/1996 | Wright |
| 5,579,149 A | 11/1996 | Moret et al. |
| 5,580,923 A | 12/1996 | Yeung et al. |
| 5,589,508 A | 12/1996 | Schlotzer et al. |
| 5,591,230 A | 1/1997 | Horn et al. |
| 5,593,441 A | 1/1997 | Lichtenstein et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,629,021 A | 5/1997 | Wright |
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,731,346 A | 3/1998 | Egberg et al. |
| 5,736,152 A | 4/1998 | Dunn et al. |
| 5,747,533 A | 5/1998 | Egberg et al. |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,817,343 A * | 10/1998 | Burke ........................... 424/489 |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,010,776 A | 1/2000 | Exsted et al. |
| 6,015,844 A | 1/2000 | Harvey et al. |
| 6,028,164 A | 2/2000 | Loomis |
| 6,040,330 A | 3/2000 | Hausheer et al. |
| 6,048,725 A | 4/2000 | Shimada et al. |
| 6,056,970 A | 5/2000 | Greenawalt et al. |
| 6,077,698 A | 6/2000 | Swan et al. |
| 6,080,442 A | 6/2000 | Yoshikawa et al. |
| 6,083,950 A | 7/2000 | Anand et al. |
| 6,090,809 A | 7/2000 | Anand et al. |
| 6,093,792 A | 7/2000 | Gross et al. |
| 6,117,911 A | 9/2000 | Grainger et al. |
| 6,120,539 A | 9/2000 | Eldridge et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,366 B1 * | 6/2001 | Popplewell .............. A23D 9/05 426/516 |
| 6,245,811 B1 | 6/2001 | Horrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,485,752 B1 | 11/2002 | Rein et al. |
| 6,491,938 B2 | 12/2002 | Kunz |
| 6,500,453 B2 | 12/2002 | Brey et al. |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang et al. |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 * | 1/2004 | Giezen et al. .................. 516/31 |
| 6,685,956 B2 | 2/2004 | Chu et al. |
| 6,696,583 B2 | 2/2004 | Koncar et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,323,189 B2 | 1/2008 | Pathak |
| 7,415,811 B2 | 8/2008 | Gottlieb et al. |
| 7,854,958 B2 | 12/2010 | Kramer |
| 7,947,015 B2 | 5/2011 | Herweck et al. |
| 8,124,127 B2 | 2/2012 | Faucher et al. |
| 8,263,102 B2 | 9/2012 | Labrecque et al. |
| 8,308,684 B2 | 11/2012 | Herweck et al. |
| 8,367,099 B2 | 2/2013 | Herweck et al. |
| 8,501,229 B2 | 8/2013 | Faucher et al. |
| 8,722,077 B2 | 5/2014 | Labrecque et al. |
| 9,000,040 B2 | 4/2015 | Faucher et al. |
| 9,012,506 B2 | 4/2015 | Faucher et al. |
| 2001/0025034 A1 | 9/2001 | Arbiser |
| 2001/0025196 A1 | 9/2001 | Chinn et al. |
| 2001/0051595 A1 | 12/2001 | Lyons et al. |
| 2002/0002154 A1 | 1/2002 | Guivarc'h et al. |
| 2002/0007209 A1 | 1/2002 | Scheerder et al. |
| 2002/0012741 A1 | 1/2002 | Heinz et al. |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0098278 A1 | 7/2002 | Bates et al. |
| 2002/0116045 A1 | 8/2002 | Eidenschink |
| 2002/0120333 A1 | 8/2002 | Keogh et al. |

(56) References Cited

U.S. PATENT DOCUMENTS

| | | |
|---|---|---|
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1* | 4/2003 | Pathak .................. 424/94.64 |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0108588 A1 | 6/2003 | Chen et al. |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0220297 A1 | 11/2003 | Berstein et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0117007 A1 | 6/2004 | Whitbourne et al. |
| 2004/0131755 A1 | 7/2004 | Zhong et al. |
| 2004/0133275 A1 | 7/2004 | Mansmann |
| 2004/0137066 A1 | 7/2004 | Jayaraman |
| 2004/0137179 A1 | 7/2004 | Matsuda et al. |
| 2004/0142094 A1 | 7/2004 | Narayanan |
| 2004/0146546 A1 | 7/2004 | Gravett et al. |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0124062 A1 | 6/2005 | Subirade |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0051544 A1 | 3/2006 | Goldmann |
| 2006/0058881 A1 | 3/2006 | Trieu |
| 2006/0067974 A1 | 3/2006 | Labrecque et al. |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1* | 6/2006 | Labhasetwar et al. ....... 424/469 |
| 2006/0158361 A1 | 7/2006 | Chou |
| 2006/0188607 A1 | 8/2006 | Schramm et al. |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0141112 A1 | 6/2007 | Falotico et al. |
| 2007/0202149 A1 | 8/2007 | Faucher et al. |
| 2007/0212411 A1 | 9/2007 | Fawzy et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0016037 A1 | 1/2008 | Enomoto et al. |
| 2008/0038307 A1 | 2/2008 | Hoffmann |
| 2008/0044481 A1* | 2/2008 | Harel .................. 424/490 |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0160307 A1* | 7/2008 | Bauchet ................ C08K 11/00 428/402 |
| 2008/0206305 A1 | 8/2008 | Herweck et al. |
| 2008/0279929 A1 | 11/2008 | Devane et al. |
| 2008/0286440 A1 | 11/2008 | Scheer |
| 2008/0289300 A1 | 11/2008 | Gottlieb et al. |
| 2009/0011116 A1 | 1/2009 | Herweck et al. |
| 2009/0047414 A1 | 2/2009 | Corbeil et al. |
| 2009/0092665 A1 | 4/2009 | Mitra et al. |
| 2009/0181074 A1 | 7/2009 | Makower et al. |
| 2009/0181937 A1 | 7/2009 | Faucher et al. |
| 2009/0208552 A1 | 8/2009 | Faucher et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2011/0045050 A1 | 2/2011 | Elbayoumi et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 | 1/2003 |
| EP | 1364628 | 11/2003 |
| EP | 1520795 | 4/2005 |
| EP | 1557183 | 7/2005 |

(56) References Cited

FOREIGN PATENT DOCUMENTS

| | | |
|---|---|---|
| EP | 2083875 | 8/2009 |
| EP | 1 402 906 | 6/2011 |
| KR | 20080025986 | 3/2008 |
| WO | WO 86/00912 | 2/1986 |
| WO | WO 90/01969 | 3/1990 |
| WO | 90/08544 A1 | 8/1990 |
| WO | WO 95/26715 | 10/1995 |
| WO | WO 97/02042 | 1/1997 |
| WO | WO 97/09367 | 3/1997 |
| WO | WO 97/13528 | 4/1997 |
| WO | WO 98/30206 | 7/1998 |
| WO | 98/46287 A2 | 10/1998 |
| WO | WO 98/54275 | 12/1998 |
| WO | WO 99/25336 | 5/1999 |
| WO | WO 00/40278 | 7/2000 |
| WO | WO 00/62830 | 10/2000 |
| WO | WO 01/24866 | 4/2001 |
| WO | WO 01/26585 | 4/2001 |
| WO | WO 01/37808 | 5/2001 |
| WO | WO 01/60586 | 8/2001 |
| WO | WO 01/66036 | 9/2001 |
| WO | WO 01/76649 | 10/2001 |
| WO | WO 02/49535 | 6/2002 |
| WO | WO 02/100455 | 12/2002 |
| WO | WO 03/000308 | 1/2003 |
| WO | WO 03/015748 | 2/2003 |
| WO | WO 03/028622 | 4/2003 |
| WO | WO 03/037397 | 5/2003 |
| WO | WO 03/037398 | 5/2003 |
| WO | WO 03/039612 | 5/2003 |
| WO | WO 03/041756 | 5/2003 |
| WO | WO 03/070125 | 8/2003 |
| WO | WO 03/092741 | 11/2003 |
| WO | WO 03/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | 2004101010 A1 | 11/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | WO 2005082434 A2 * | 9/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | 2008/010788 A2 | 1/2008 |
| WO | 2008/016664 A2 | 2/2008 |
| WO | WO 2008/057328 | 5/2008 |
| WO | 2010/042134 A1 | 4/2010 |
| WO | 2010/042241 A1 | 4/2010 |
| WO | WO 2012/009707 | 1/2012 |

OTHER PUBLICATIONS

"Cure" in Academic Press Dictionary of Science and Technology (1992). one page.

"Polymerization" Merriam-Webster Online Dictionary, retrieved from <www.merriam-webster.com> on Dec. 13, 2009; Merriam-Webster's Inc. 2009; pp. 1.

Ahuja et al. Journal of Indian Pediatric Surgery 2002 7:15-20.

Autosuture, "ParietexTM Composite OS Series Mesh," retrieved online at http://www.autosuture.com/AutoSuture/pagebuilder.aspx?topicID=135734&breadcrumbs=135 601:0 2007, two pages.

Binder et al., "Chromatographic Analysis of Seed Oils. Fatty Acid Composition of Castor Oil," The Journal of the American Oil Chemists' Society, vol. 39:513-517 (1962).

CECW-EE, "Ch. 4: Coating Types and Characteristics," Engineering and Design—Painting: New Construction and Maintenance, pp. 4-1 to 4-24 (1995).

De Scheerder, Ivan K. et al. "Biocompatibility of polymer-coated oversized metallic stents implanted in normal porcine coronary arteries," Atherosclerosis, vol. 114:105-114.

Drummond, Calum J. et al., "Surfactant self-assembly objects as novel drug delivery vehicles," Current Opinion in Colliod & Interface Science, vol. 4:449-456 (2000).

Engstrom, Sven, "Drug Delivery from Cubic and Other Lipid-water Phases," Lipid Technology, vol. 2(2):42-45 (1990).

Guler, et al. "Some empirical equations for oxopolymerization of linseed oil," Progress in Organic Coatings, vol. 51:365-371 (2004).

Hwang, Chao-Wei et al, "Physiological Transport Forces Govern Drug Distribution for Stent-Based Delivery," Circulation, vol. 104:600-605 (2001).

Jonasson, Lena et al., "Cyclosporon A inhibits smooth muscle proliferation in the vascular response to injury," Proc. Natl. Acad. Sci, USA, vol. 85: 2303-2306 (1988).

Mallegol et al., "Drier Influence on the Curing of Linseed Oil," Progress in Organic Coatings 39:107-113 (2000).

Morse, Richard "Molecular Distillation of Polymerized Drying Oils," Industrial and Engineering Chemisry 33:1039-1043 (1941).

Oberhoff, Martin et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).

Ogunniyi, D.S., "Castor oil: A vital industrial raw material," Biosource Technology, vol. 97: 1086-1091 (2006).

Redman, L.V. et al., "The drying rate of raw paint oils—a comparison," The Journal of Industrial and Engineering Chemistry, vol. 5: 630-636 (1913).

Rutkow, Ira M. et al., "'Tension-free' inguinal herniorrhaphy: A preliminary report on the 'mesh plug' technique," Surgery, vol. 114:3-8 (1993).

Salu, Koen J. et al, "Addition of cytochalasin D to a biocompatible oil stent coating inhibits intimal hyperplasia in a porcine coronary model," Coronary Artery Disease, vol. 14(8):545-555 (2003).

Scheller, Bruno et al, "Addition of Paclitaxel to Contrast Media Prevents Restenosis After Coronary Stent Implantation," Journal of the American College of Cardiology, vol. 42(8):1415-1420 (2003).

Shahidi, Fereidoon ed.; "Bailey's Industrial Oil and Fats Products" 2005; John Wiley and Sons; vol. 5, Edible Oil and Fat Products: Processing Technologies, pp. 1-15.

Van der Giessen, Willem J. et al, "Marked Inflammatory Sequelae to Implantation of Biodegradable and Nonbiodegradable Polymers in Porcine Coronary Arteries," Circulation, vol. 94:1690-1697 (1996).

Websters Dictionary Online, Accessed on Feb. 13, 2009, entry for "polymer" p. 1 of 1.

Wikipedia, "Sirolimus," pp. 1-13, available online at http://en.wikipedia.org/wiki/Sirolimus, date accessed May 11, 2011.

Encylopedia Britannica Online, "Surface Coating", available online at http://www.britannica.com/EBchecked/topic/575029/surface-coating>, date accessed Jun. 17, 2011. p. 1-9.

International Search Report for International Application PCT/US05/034601, dated Apr. 10, 2006.

International Search Report for International Application PCT/US05/034610, dated Mar. 16, 2006.

International Search Report for International Application PCT/US05/034614, dated Aug. 29, 2006.

International Search Report for International Application PCT/US05/034615, dated May 16, 2006.

International Search Report for International Application PCT/US05/034678, dated Aug. 28, 2006.

International Search Report for International Application PCT/US05/034681, dated Jul. 26, 2006.

International Search Report for International Application PCT/US05/034682, dated Jul. 20, 2006.

International Search Report for International Application PCT/US05/034836, dated Jul. 6, 2006.

International Search Report for International Application PCT/US05/034941, dated May 4, 2006.

International Search Report for International Application PCT/US06/037184, dated Feb. 22, 2007.

(56) References Cited

OTHER PUBLICATIONS

International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Non-final Office Action for U.S. Appl. No. 11/236,908 (listed on SB/08 as US 2006/0067974), mailed Mar. 25, 2006.
Final Office Action for U.S. Appl. No. 11/236,908 (listed on SB/08 as US 2006/0067974), mailed May 17, 2011.
Non-final Office Action for U.S. Appl. No. 11/236,908 (listed on SB/08 as US 2006/0067974), mailed Aug. 24, 2009.
Final Office Action for U.S. Appl. No. 11/236,943 (listed on SB/08 as US 2006/0067975), mailed Dec. 23, 2009.
Non-Final Office Action for U.S. Appl. No. 11/236,943 (listed on SB/08 as US 2006/0067975), mailed Mar. 5, 2009.
Non-final Office Action for U.S. Appl. No. 11/236,977 (listed on SB/08 as US 2006/0088596), mailed Aug. 3, 2009.
Final Office Action for U.S. Appl. No. 11/237,263 (listed on SB/08 as US 2006/0110457), mailed Jul. 7, 2010.
Non-final Office Action for U.S. Appl. No. 11/237,263 (listed on SB/08 as US 2006/0110457), mailed Oct. 7, 2009.
Final Office Action for U.S. Appl. No. 11/237,264 (listed on SB/08 as US 2006/0067983), mailed Jun. 2, 2010.
Non-final Office Action for U.S. Appl. No. 11/237,264 (listed on SB/08 as US 2006/0067983), mailed Oct. 5, 2009.
Final Office Action for U.S. Appl. No. 11/701,799 (listed on SB/08 as US 2008/0109017), mailed Nov. 23, 2010.
Non-final Office Action for U.S. Appl. No. 11/237,420 (listed on SB/08 as US 2006/0078586), mailed Mar. 5, 2009.
Final Office Action for U.S. Appl. No. 11/237,420 (listed on SB/08 as US 2006/0078586), mailed Nov. 4, 2009.
Non-final Office Action for U.S. Appl. No. 11/237,420 (listed on SB/08 as US 2006/0078586), mailed Dec. 6, 2010.
Non-final Office Action for U.S. Appl. No. 11/238,532 (listed on SB/08 as US 2006/0067976, mailed Mar. 30, 2009.
Final Office Action for U.S. Appl. No. 11/238,532 (listed on SB/08 as US 2006/0067976), mailed Sep. 9, 2009.
Final Office Action for U.S. Appl. No. 11/238,554 (listed on SB/08 as US 2006/0121081), mailed May 12, 2010.
Non-final Office Action for U.S. Appl. No. 11/238,554 (listed on SB/08 as US 2006/0121081), mailed Oct. 9, 2009.
Final Office Action for U.S. Appl. No. 11/238,554 (listed on SB/08 as US 2006/0121081), mailed May 1, 2009.
Non-final Office Action for U.S. Appl. No. 11/238,554 (listed on SB/08 as US 2006/0121081), mailed Jul. 25, 2008.
Non-final Office Action for U.S. Appl. No. 11/238,564 (listed on SB/08 as US 2006/0083768), mailed Apr. 16, 2008.
Final Office Action for U.S. Appl. No. 11/238,564 (listed on SB/08 as US 2006/0083768), mailed Aug. 6, 2009.
Non-final Office Action for U.S. Appl. No. 11/239,555 (listed on SB/08 as US 2006/0067977), mailed Mar. 30, 2009.
Non-final Office Action for U.S. Appl. No. 11/525,328 (listed on SB/08 as US 2007/0084144), mailed Apr. 30, 2007.
Non-final Office Action for U.S. Appl. No. 11/525,390 (listed on SB/08 as US 2007/0071798), mailed Jul. 14, 2010.
Final Office Action for U.S. Appl. No. 11/525,390 (listed on SB/08 as US 2007/0071798), mailed Feb. 21, 2011.
Final Office Action for U.S. Appl. No. 11/582,135 (listed on SB/08 as US 2007/0202149), mailed May 12, 2011.
Non-final Office Action for U.S. Appl. No. 11/582,135 (listed on SB/08 as US 2007/0202149), mailed Nov. 9, 2010.
Non-final Office Action for U.S. Appl. No. 11/582,135 (listed on SB/08 as US 2007/0202149), mailed Jan. 6, 2010.
Non-final Office Action for U.S. Appl. No. 11/582,135 (listed on SB/08 as US 2007/0202149), mailed May 12, 2009.
Non-final Office Action for U.S. Appl. No. 11/701,799 (listed on SB/08 as US 2008/0109017), mailed Apr. 12, 2010.
Non-final Office Action for U.S. Appl. No. 11/978,840 (listed on SB/08 as US 2008/0118550), mailed Dec. 3, 2010.
Non-final Office Action for U.S. Appl. No. 11/980,155 (listed on SB/08 as US 2008/0113001) mailed Mar. 24, 2011.
Non-final Office Action for U.S. Appl. No. 12/075,223 (listed on SB/08 as US 2008/0206305), mailed Dec. 8, 2010.
Non-final Office Action for U.S. Appl. No. 12/325,546 (listed on SB/08 as US 2009/0181937), mailed Feb. 25, 2010.
Final Office Action for U.S. Appl. No. 12/325,546 (listed on SB/08 as US 2009/0181937), mailed Aug. 31, 2010.
Non-final Office Action for U.S. Appl. No. 12/364,763 (listed on SB/08 as US 2009/0208552), mailed Dec. 11, 2009.
Final Office Action for U.S. Appl. No. 12/364,763 (listed on SB/08 as US 2009/0208552), mailed Sep. 21, 2010.
Final Office Action for U.S. Appl. No. 11/978,840 (listed on SB/08 as US 2008/0118550), mailed Jun. 22, 2011.
Interview summary for U.S. Appl. No. 11/236,908 (listed on SB/08 as US 2006/0067974), mailed May 5, 2009.
Interview summary for U.S. Appl. No. 11/236,908 (listed on SB/08 as US 2006/0067974), mailed Dec. 2, 2010.
Interview summary for U.S. Appl. No. 11/237,420 (listed on SB/08 as US 2006/0078586), mailed May 5, 2009.
Interview summary for U.S. Appl. No. 11/582,135 (listed on SB/08 as US 2007/0202149), mailed Dec. 7, 2010.
Interview summary for U.S. Appl. No. 12/325,546 (listed on SB/08 as US 2009/0181937), mailed Dec. 2, 2010.
Interview summary for U.S. Appl. No. 12/364,763 (listed on SB/08 as US 2009/0208552), mailed Dec. 2, 2010.
Crivello et al., "Epoxidized triglycerides as renewable monomers in photoinitiated cationic polymerization," Chem. Mater, 1992:692-699.
Timir-Balizsy et al., "Chemical Principals of Textile Conservation," Oxford: Elsevier Science Ltd., 1998:117-119.
Supplementary European Search Report in Application No. EP 05 80 4291, dated Jul. 26, 2011.
Supplementary European Search Report for Application No. EP 05 80 2894, dated Jul. 27, 2011.
Supplementary European Search Report in Application No. EP 05 85 8430, dated Aug. 18, 2011.
Supplementary European Search Report in Application No. 05 800 844, dated Aug. 19, 2011.
Non-final Office Action for U.S. Appl. No. 11/525,390 (listed on SB/08 as US 2007/0071798), mailed Jul. 11, 2011.
Final Office Action for U.S. Appl. No. 11/237,420 (listed on SB/08 as US 2006/0078586), mailed Jul. 13, 2011.
Final Office Action for U.S. Appl. No. 12/075,223 (listed on SB/08 as US 2008/0206305), mailed Aug. 11, 2011.
Non-Final Office Action for U.S. Appl. No. 11/701,799 (listed on SB/08 as US 2008/0109017), mailed Aug. 17, 2011.
Non-Final Office Action for U.S. Appl. No. 11/582,135, mailed Oct. 14, 2011.

(56) References Cited

OTHER PUBLICATIONS

Non-Final Office Action for U.S. Appl. No. 11/236,908 (listed on SB/08 as US 2006-0067974), mailed Dec. 2, 2011.
Non-Final Office Action for U.S. Appl. No. 12/182,261 (listed on SB/08 as US 2009/0047414), mailed Dec. 21, 2011.
Notice of Allowance for U.S. Appl. No. 11/582,135 (listed on SB/08 as US 2007/0202149), mailed Jan. 9, 2012.
Non-Final Office Action for U.S. Appl. No. 12/182,165 (listed on SB/08 as US 2009/0011116), mailed Jan. 5, 2012.
Final Office Action for U.S. Appl. No. 11/701,799 (listed on SB/08 as US 2008/0109017), mailed Feb. 13, 2012.
Non-Final Office Action for U.S. Appl. No. 12/581,582 (listed on SB-08 as US 2010-0183697), mailed Mar. 14, 2012.
Final Office Action for U.S. Appl. No. 12/182,261 (listed on SB-08 as US-2009-0047414), mailed Apr. 30, 2012.
Notice of Allowance for U.S. Appl. No. 11/236,908 (listed on SB-08 as US-2006-0067974), mailed May 11, 2012.
Ackman, R.G., "Fish Oils", *Bailey's Industrial Oil and Fat Products*, 6th Edition, 279-317 (2005).
Andes, et al. "Antiproliferative Strategies for the Treatment of Vascular Proliferative Disease", *Current Vascular Pharmacology*, 1)1 : 85-98 (2003).
Jorge, N., "Grasas y Aceites", 48(1): 17-24, (1997).
Lipids, Chapter 19, pp. 1-12 (2002).
Winter, et al., "Physical and Chemical Gelation" *Encyclopedia of Materials—Science and Technology*, vols. 1-11: 6691-6999 (2001).
Supplementary European Search Report for Application No. EP 12004057, dated Apr. 10, 2013.
Advisory Action for U.S. Appl. No. 12/581,582 (listed on SB-08 as U.S. Publication No. 2010-0183697), dated Nov. 14, 2012.
Notice of Allowance for U.S. Appl. No. 11/525,390 (listed on SB-08 as U.S. Publication No. US-2007-0071798), dated Nov. 20, 2012.
Notice of Allowance for U.S. Appl. No. 11/525,390 (listed on SB/08 as US-2007/0071798), mailed Nov. 30, 2012.
Non-Final Office Action for U.S. Appl. No. 13/404,487 (listed on SB-08 as US 2012-0213839), dated Dec. 20, 2012.
Non-Final Office Action for U.S. Appl. No. 13/184,512 (listed on SB-08 as 2012-0016038), dated Jan. 31, 2013.
Non-Final Office Action for U.S. Appl. No. 11/978,840 (listed on SB-08 as U.S. No. US-2008-0118550), dated Feb. 19, 2013.
Non-Final Office Action for U.S. Appl. No. 13/682,991 (listed on SB-08 as U.S. Publication No. US-2013-0074452), dated Mar. 18, 2013.
Notice of Allowance for U.S. Appl. No. 13/404,487 (listed on SB-08 as U.S. Publication No. US-2012-0213839), dated Apr. 2, 2013.
Non-Final Office Action for U.S. Appl. No. 11/236,943 (listed on SB-08 as U.S. Publication No. US-2006-0067975), dated Apr. 22, 2013.
Final Office Action for U.S. Appl. No. 13/184,512 (listed on SB-08 as U.S. Publication No. U.S. 2012-0016038), date Jun. 25, 2013.
Non-Final Office Action for U.S. Appl. No. 11/237,264 (listed on SB-08 as U.S. Publication No. US-2006-0067983), dated Jul. 3, 2013.
Non-Final Office Action for U.S. Appl. No. 13/593,656 (listed on SB-08 as U.S. Publication No. US-2012-03115219), dated Jul. 15, 2013.
Notice of Allowance for U.S. Appl. No. 13/682,991 (listed on SB-08 as U.S. Publication No. US 2013-0074452), dated Aug. 1, 2013.
Notice of Allowance for U.S. Appl. No. 11/978,840 (listed on SB-08 as U.S. Publication No. US-2008-0118550), dated Aug. 6, 2013.
International Search Report for International Application PCT/US2011/44292, mailed Dec. 6, 2011.
European Supplemental Search Report for European Application 09819594.4, mailed Aug. 14, 2012.
European Supplemental Search Report for European Application 08877338.7, mailed Aug. 16, 2012.
Final Office Action for U.S. Appl. No. 12/182,165, (listed on SB/08 as US 2009-0011116), mailed Apr. 6, 2012.
Notice of Allowance for U.S. Appl. No. 12/182,261 (listed on SB/08 as US-2009-0047414), mailed Jul. 23, 2012.
Final Office Action for U.S. Appl. No. 12/581,582 (listed on SB/08 as US 2010-0183697), mailed Aug. 29, 2012.
Non-Final Office Action for U.S. Appl. No. 11/525,390 (listed on SB/08 as US-2007-0071798), mailed Oct. 4, 2012.
Notice of Allowance for U.S. Appl. No. 11/237,264 (listed on SB-08 as U.S. Publication No. US-2006-0067983), dated, Mar. 27, 2014.
Notice of Allowance for U.S. Appl. No. 11/237,263 (listed on SB-08 as U.S. Publication No. US-2006-0110457), dated Mar. 27, 2014.
Mallegol, "Long-Term Behavior of Oil-Based Varnishes and Paints Photo-and Thermooxidation of Cured Linseed Oil", *Journal of the American Oil Chemists' Society*, 77:257-263 (2000).
Non-Final Office Action for U.S. Appl. No. 11/237,420 (listed on SB-08 as U.S. Publication No. US-2006-0078586), dated Nov. 12, 2013.
Non-Final Office Action for U.S. Appl. No. 12/075,223 (listed on SB-08 as U.S. Publication No. US-2008-0206305), dated Nov. 12, 2013.
Non-Final Office Action for U.S. Appl. No. 11/980,155 (listed on SB-08 as U.S. Publication No. US-2008-0113001), dated Nov. 12, 2013.
Final Office Action for U.S. Appl. No. 11/236,943 (listed on SB-08 as U.S. Publication No. US-2006-0067975), dated Dec. 4, 2013.
Final Office Action for U.S. Appl. No. 11/237,264 (listed on SB-08 as U.S. Publication No. US-2006-0067983), dated Dec. 17, 2013.
Notice of Allowance for U.S. Appl. No. 13/593,656 (listed on SB-08 as U.S. Publication 2012-03115219), dated Jan. 24, 2014.
International Search Report for International Application PCT/US2013/044653, dated Sep. 4, 2013.
Non-Final Office Action for U.S. Appl. No. 13/184,512, dated Oct. 10, 2014.
Non-Final Office Action for U.S. Appl. No. 12/075,223, dated Oct. 29, 2014.
Supplementary European Search Report for Application No. EP 10825447, dated Mar. 31, 2014.
Non Final Office Action for U.S. Appl. No. 12/325,546 (listed on SB-08 as U.S. Publication No. US-2009-0181937), dated Apr. 22, 2014.
Non Final Office Action for U.S. Appl. No. 12/364,763 (listed on SB-08 as U.S. Publication No. US-2009-0208552), dated Apr. 23, 2014.
Non-Final Office Action for U.S. Appl. No. 11/980,155, dated Nov. 7, 2014.
Notice of Allowance for U.S. Appl. No. 12/364,763 (listed on SB-08 as U.S. Publication No. US-2009-0208552), dated Dec. 5, 2014.
Notice of Allowance for U.S. Appl. No. 12/325,546 (listed on SB-08 as U.S. Publication No. US-2009-0181937), dated Dec. 8, 2014.
Non-Final Office Action for U.S. Appl. No. 13/843,068, dated Sep. 29, 2014.
Notice of Allowance for U.S. Appl. No. 11/236,943 (listed on SB-08 as U.S. Publication No. US-2006-0067975), dated Oct. 6, 2014.
Uchida, et al., "Swelling Process and Order-Disorder Transition of Hydrogel Containing Hydrophobic Ionizable Groups", *Macromolecules*, 28, 4583-4586 (1995).
Gutfinger, et al., "Polyphenols in Olive Oils", *Journal of the American Oil Chemists Society*, 58(11): 966-968 (1981).
Portilla, et al., "Prevention of Peritoneal Adhesions by Intraperitoneal Administration of Vitamin E: An Experimental Study in Rats", *Diseases of the Colon and Rectum*, 47: 2157-2161 (2005).
Sano, et al., "A controlled Trial of Selegiline, Alpha-Tocopherol, or Both as Treatment for Alzheimer's Disease", *The New England Journal of Medicine*, 336; 1216-1222 (1997).
Non Final Office Action for U.S. Appl. No. 12/581,582 (listed on SB-08 as U.S. Publication 2010-0183697), dated May 29, 2014.
Non-Final Office Action for U.S. Appl. No. 13/943,489, dated Jul. 1, 2014.
Final Office Action for U.S. Appl. No. 11/980,155, dated Jul. 21, 2014.
Final Office Action for U.S. Appl. No. 11/237,420, dated Jul. 22, 2014.
Non-Final Office Action for U.S. Appl. No. 11/701,799, dated Jul. 22, 2014.

(56) References Cited

OTHER PUBLICATIONS

Final Office Action for U.S. Appl. No. 12/075,223, dated Jul. 22, 2014.
Final Office Action for U.S. Appl. No. 13/843,068, dated Apr. 23, 2015.
Final Office Action for U.S. Appl. No. 13/184,512, dated Apr. 28, 2015.
Final Office Action for U.S. Appl. No. 11/701,799, dated Mar. 12, 2015.
Final Office Action for U.S. Appl. No. 12/581,582, dated Jan. 8, 2015.
Non-Final Office Action for U.S. Appl. No. 11/237,420, dated Jan. 21, 2015.
Notice of Allowance for U.S. Appl. No. 13/943,489, mailed Jan. 29, 2015.
Wicks et al. Organic Coatings:Science and Technology 1999 New York:Wiley Interscience p. 258-267.
Mills et al. Oils and Fats. "The Organic Chemistry of Museum Objects" London:Buttersworth and Co. 1987, p. 26-40.
Erhardt Paints Based on Drying Oil Media. Painted Wood: History & Conservation. Ed. Berland Singapore: The J. Paul Getty Trust 1998. p. 17-32.
Wexler et al. Chemical Reviews 1964 64(6):591-611.
Polymer—The Chambers 21st Century Dictionary M. Robinson and G. Davidson (Eds.), London, United Kingdom: Chambers Harrap. Retrieved from http://search.credoreference.com/content/entry/chambdict!polymer/0.
Polymer—Academic Press Dictionary of Science and TechnologyC. Morris (Ed.), Academic Press Dictionary of Science and Technology. Oxford, United Kingdom: Elsevier Science & Technology. Retrieved from http://search.credoreference.com/content/entry/apdst!polymer/0.
Falagas et al. European Society of Clinical Microbiology and Infection Diseases 2005 11:3-8.
Bimbo (INFORM 1998 9(5):473-483.
Article on Lead, Centers for Disease Control and Prevention, Nov. 2009, 2 pages.
American heritage desk dictionary, 1981, p. 799, 2 pages.
Wikipedia, Sunflower oil, https://en.wikipedia.org/wiki/Sunflower_oil, accessed Jul. 23, 2015 in related U.S. Appl. No. 14/252,671, pp. 1-7.
Esoteric Oils, Peppermint essential oil information, http://www.essentialoils.co.za/essential-oils/peppermint.htm, accessed Jul. 23, 2015 in related U.S. Appl. No. 14/252,671, pp. 1-7.
Orthomolecular, Fish Oil, Jun. 29, 2004, http://orthomolecular.org/nutrients/fishoil.html, accessed Jul. 22, 2015 in related U.S. Appl. No. 14/252,671, p. 1.
H. Fineberg et al., Industrial Use of Fish Oils, pp. 222-238, http://spo.nmfs.noaa.gov/Circulars/CIRC278.pdf, downloaded Aug. 3, 2015.
Lewis, Richard J., Sr., Hawley's Condensed Chemical Dictionary, 2001, pp. 308, 309 and 896-898, 14th edision, John Wiley & Sons, Inc., New York.
Webster's II New College Dictionary (1995), 1075, Houghton Mifflin Company, New York, US.
Polymers made from multiple monomers, A Natural Approach to Chemistry, Chapter 8, 241, http://lab-aids.com/assets/uploads/NAC/NAC_student_book/Texas%20Student%20Edition%20253.pdf (downloaded Dec. 3, 2015).
Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).
SepraFilm Adhesion Barrier package insert (Genzyme Biosurgery 2008).
Sannino, Alessandro, et al., Biodegradeable Cellulose-based Hydrogels: Design and Applications, 2 MATERIALS, pp. 353-373, 2009.
Heinz, Thomas, Carboxymethyl Ethers of Cellulose and Starch—A Review, Center of Excellence for Polysaccharide Research, Friedrich Schiller University of Jena (Germany), pp. 13-29, 2005.
Omidian, H. et al., Swelling Agents and Devices in Oral Drug Delivery, J. Drug. Del. Sci. Tech., No. 18, vol. 2, 2008, pp. 83-93.
Kamel, S. et al., Pharmaceutical Significance of Cellulose: A Review, Express Polymer Letters vol. 2, No. 11, 2008, pp. 758-778.
Adel, A. M. et al., Carboxymethylated Cellulose Hydrogel: Sorption Behavior and Characterization, Nature and Science, No. 8, vol. 8, 2010, pp. 244-256.
Bacteria in Water, The USGS Water Science School, http://water.usgs.gov/edu/bacteria.html (downloaded Nov. 9, 2015).
Novotny, L. et al., Fish: a potential source of bacterial pathogens for human beings, Vet. Med.—Czech, 49, 2004, vol. 9, pp. 343-358.
Allergies, Asthma and Allergy Foundation of America (2011), http://www.aafa.org/page/types-of-allergies,aspx (downloaded Oct. 5, 2015).
Sicherer, Scott H., Food Allergies: A Complete Guide for Eating When Your Life Depends on it, 2013, 15, Johns Hopkins University Press, Baltimore, MD, USA.
Omega-3 DHA—The Problem May Be the Quality of Your Fish Oil, Not Your Allergy to Fish, Fatty Acids Hub, http://www.fattyacidshub.com/fatty-acids/omega-3-dha/ (downloaded Nov. 10, 2015).
Soy Allergy, Asthma and Allergy Foundation of America (2005), http://www.aafa.org/display.cfm?id=9&sub=20&cont=522 (downloaded Nov. 10, 2015).
Refined soybean oil not an allergen, say food scientists, FOOD navigator-usa.com (2005), http://www.foodnavigator-usa.com/content/view/print/127438 (downloaded Nov. 10, 2015).
Yahyaee, R. et al., Waste fish oil biodiesel as a source of renewable fuel in Iran, Renewable and Sustainable Energy Reviews, 2013, pp. 312-319, 17, Elsevier Ltd.
Biological evaluation of medical devices—Part 1: Evaluation and testing, International Standard ISO 109931-1, Aug. 1, 2003, Third Edition, Switzerland.
Mayo Clinic (http://www.mayoclinic.org/drugs-supplements/omega-3-fatty-acids-fish-oil-alpha-linolenic-acids/safety/nrb-20059372?p=1 (downloaded Sep. 28, 2015).
Milk allergy, at http://www.mayoclinic.org/diseases-conditions/milk-allergy/basics/definition/con-20032147?p=1 ;downloaded Jul. 29, 2015).
Soy allergy, at http://www.mayoclinic.org/diseases-conditions/soy-allergy/basics/definition/con-20031370?p=1 ;downloaded Jul. 29, 2015).
F.D. Gunstone, Fatty Acid and Lipid Chemistry 72 (1999).
Hawley's Condensed Chemical Dictionary 315, 316, 332, 333, 334, 825 and 826 (2001).
Hutlin, Herbert O. et al., Chemical Composition and Stability of Fish Oil (International Association of Fish Meal Manufacturers Apr. 10, 1991).
F.V.K Young, The Chemical & Physical Properties of Crude Fish Oils for Refiners and Hydrogenators, 18 Fish Oil Bulletin 1-18 (1986).
Karrick, Neva L., Nutritional Value of Fish Oils as Animal Feed, Circular 281 (Fish and Wildlife Service Bureau of Commercial Fisheries 1967), reprinted from M.E. Stansby (ed.), Fish Oils 362-382 (Avi Publishing Company 1967).
Luley et al., Fatty acid composition and degree of peroxidation in fish oil and cod liver oil preparations, Arzneimittelforschung. Dec. 1998, vol. 38, No. 12, pp. 1783-1786.
Drying Oil, http://en.wikipedia.org/wiki/drying_oil (downloaded Jun. 28, 2013).
Szebeni et al., "Complement Activation by Cremophor EL as a Possible Contributor to Hypersensitivity to Paclitaxel: an In Vitro Study", Journal of the National Cancer Institute, 1998, vol. 90, No. 4, pp. 300-306.
Birsan, et al., "The novel calcineurin inhibitor ISA247: a more potent immunosuppressant than cyclosporine in vitro", Transpl. Int., 2005, vol. 17, pp. 767-771.
About.com, "Orthopedics, Synvisc injections," retrieved online at http://orthopedics.about.com/cs/treatment/a/synvisc_2.htm (2005).

(56) References Cited

OTHER PUBLICATIONS

Cath Lab Digest, "Olive Oil Emulsion Helps With Problem Heart Arteries", retrieved online at http://www.cathlabdigest.com/displaynews.cfm?newsid=0103073 (2007).
Doctor's Guide to Medical and Other News, "AAOS Meeting: Synvisc Delays Total Knee Replacement in Osteoarthritis Patients", retrieved online at http://www.docguide.com/dg.nsf/PrintPrint/4585EC355198EEF08525670E006B10FF (1999).
Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington Convention Center, Washington, D.C.
Novavax, retrieved online at http://www.novavax.com/go.cfm?do=Page.View&pid=3 (2006).
Orthovisc, "New Treatment Option is Potential Alternative to OTC Pain Medications for Osteoarthritis of the Knee" retrieved online at http://www.jnj.com/innovations/new_features/ORTHOVISC.htm:sessionid=33N2RBQDV0DZKCQPCCEGU3AKB2IIWTT1 (2006).
Orthovisc, "What is Orthovisc®?" retrieved online at http://www.orthovisc.com/xhtmlbgdisplay.jhtml?temname=about_orthovisc (2005).
Orthovisc, "Your Knees and Osteoarthritis", retrieved online at http://www.orthovisc.com/xhtmlbgdisplay.jhtml?temname=understanding_knee_oa (2003).
Orthovisc, "What to expect from your treatment," retrieved online at http://www.orthovisc.com/xhtmlbgdisplay.jhtml?temname=what_to_expect (2007).
Orthovisc, "Tools and Resources for Managing Your Osteoarthritis", retrieved online at http://www.orthovisc.com/khtmlbgdisplay.jhtml?itemname=patient_resources (2007).
Pohibinska, A., et al., "Time to reconsider saline as the ideal rinsing solution during abdominal surgery", The American Journal of Surgery, vol. 192, pp. 281-222 (2007).
Singh, Alok, et al., "Facilitated Stent Delivery Using Applied Topical Lubrication", Catherization and Cardiovascular Interventions, vol. 69, pp. 218-222 (2007).
Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (!387).
Hortolam, Juliane G., et al., "Connective tissue diseases following silicone breast implantation: where do we stand?", Clinics, 2013, vol. 3, p. 281.
Lidar, M. et al., "Silicone and scleroderma revisited", Lupus, 2012, vol. 21, pp. 121-127.
Swanson, Danielle, et al., Omega-3 Fatty Acids EPA and DHA: Health Benefits Throughout Life, 3 Advances in Nutrition 1-7 (American Society for Nutrition 2012).
Triglycerides, https://www.lipid.org/sites/default/files/triglycerides.pdf (downloaded Sep. 24, 2015).
Fish Oil Triglycerides vs. Ethyl Esters: A Comparative Review of Absorption, Stability and Safety Concerns (Ascenta Health Ltd. 2010 at http://www.ascentaprofessional.com/science/articles/fish-oil-triglycerides-vs-ethyl-esters (downloaded Sep. 24, 2015).
Fats & Oils (2008) at http://scifun.chem.wisc.edu/chemweek/pdf/fats&oils.pdf (downloaded Sep. 24, 2015).
Web article from http://www.buchi.com, "Slip Melting Point Determination of Palm Stearin", 1 page.

\* cited by examiner

0   No fibrosis adherent to dura
1   1% to 30% of dura at injury site loosely adhered
2   31% to 70% of dura at injury site densely adhered
3   >70% of dura at injury site densely adhered

FATTY-ACID BASED PARTICLES

BACKGROUND OF THE INVENTION

The health benefits of certain fatty acids are well-documented. For example, the omega-3 fatty acids are essential for heart health and can be effective in lowering LDL cholesterol levels in the body, stopping the buildup of fatty deposits (triglycerides) in the arteries, and increasing the body's HDL cholesterol levels in the blood.

Omega-3 and omega-6 fatty acids are also known as essential fatty acids because they are important for maintaining good health, even though the human body cannot produce such fatty acids. As such, omega-3 and omega-6 fatty acids must be obtained from external sources, such as fish oil. Omega-3 fatty acids include eicosapentaenoic acid (EPA), docosahexanoic acid (DHA), and alpha-linolenic acid (ALA). EPA and DHA both have anti-inflammatory effects and wound healing effects within the human body.

Fatty acids are reported to have utility as a coating, stand alone material, or formulation ingredient in the delivery of an active pharmaceutical ingredient (see, e.g., US Patent Application Publication Nos. 2006-0067983, 20070202149 and 20080207756). Materials and constructs composed of fatty acids have demonstrated reduced inflammation and improved healing in-vivo. Alternate physical forms of fatty acids, such as particles, either with or without an active pharmaceutical ingredient, would provide an additional means of delivering fatty acids and/or pharmaceutical ingredients.

SUMMARY OF THE INVENTION

Accordingly, there remains a need for delivery of fatty acids to subjects, especially for therapeutic applications (e.g., anti-inflammatory applications). Certain embodiments of the present invention provide fatty acid-based particles. The fatty acid-based particles can be used in a variety of therapeutic settings, such as the delivery of health-benefiting omega-3 fatty acids to a target area. The particles can be associated with a therapeutic agent, and therefore can be used to deliver the therapeutic agent in a controlled manner. The particles have the advantage of a high surface area; as such, a large quantity of therapeutic agent can be loaded onto the particles for delivery to a subject. In addition, the therapeutic loaded fatty acid-based particles can be used in conjunction with medical devices (e.g., vascular grafts, hernia mesh, thin films, stents, etc.). Fatty acid-based particles (with or without a therapeutic agent) also can be loaded into fatty acid based liquids (e.g., fish oil) or gels (e.g., partially cured fish oil) to create a suspension or an emulsion.

Thus, in one aspect, the invention is directed toward a method of forming fatty acid particles comprising: associating a cross-linked fatty acid-derived biomaterial with a cryogenic liquid; and fragmenting the biomaterial/cryogenic liquid composition, such that fatty acid particles are formed. In one embodiment, the source of the cross-linked fatty acid-derived biomaterial is a fish oil, e.g., a fish oil that has been heated or exposed to UV-radiation in order to cross link some or all of the fatty acids of the fish oil.

In one embodiment of the method, the step of associating the cross-linked fatty acid-derived biomaterial with a cryogenic liquid comprises at least one of suspending, submerging, and surrounding the cross-linked fatty acid-derived biomaterial. In another embodiment, the cryogenic liquid comprises liquid nitrogen. The cross-linked fatty acid-derived biomaterial/cryogenic liquid composition can be fragmented using one or more of grinding, shearing, shocking, shattering, granulating, pulverizing, shredding, crushing, homogenizing, sonicating, vibrating, and/or milling. The cryogenic liquid can be substantially removed by evaporation, either before fragmentation or after the particles are formed.

The cross-linked, fatty acid-derived biomaterial can comprise an oil that may be natural or derived from synthetic sources. The cross-linked, fatty acid-derived biomaterial can comprise a biological oil, such as an oil containing at least one lipid or omega-3 fatty acid, such as a fish oil. The fish oil further can include vitamin E. As described herein, the fish oil is exposed to heating and/or UV irradiation to form a cross-linked, fatty acid-derived biomaterial (e.g., gel). In one embodiment, before being associated with a cryogenic liquid, the cross-linked material is in the form of a film. In another embodiment, the film is coarsely ground prior to association with the cryogenic liquid.

When the cross-linked, fatty acid-derived biomaterial is in the form of a film, a therapeutic agent can be loaded into the film before particle formation, during particle formation, or after particle formation. In still another embodiment, the film is coated with a therapeutic agent/solvent mixture. The therapeutic agent can be dissolved in a solvent, such as methanol or ethanol, and the therapeutic agent/solvent mixture can be applied to the film, e.g., by dipping or spraying.

Once prepared, the fatty acid particles can be soaked in a therapeutic agent dissolved in solvent, such as hexane, isopar, water, ethanol, methanol, proglyme, methylene chloride, acetonitrile, acetone, or MEK, and the solvent can be substantially removed, resulting in fatty acid particles associated with a therapeutic agent.

The particles, either alone or loaded with a therapeutic agent, can then be used for controlled and targeted delivery in vivo. Thus, in various embodiments, the present methods facilitate increasing the utility of a therapeutic agent, e.g., increased bioavailability, and improvement in release profile from a sustained release formulation.

The therapeutic agent used herein can be one or more of an antioxidant, anti-inflammatory agent, anti-coagulant agent, drug to alter lipid metabolism, anti-proliferative, anti-neoplastic, tissue growth stimulant, functional protein/factor delivery agent, anti-infective agent, imaging agent, anesthetic agent, chemotherapeutic agent, tissue absorption enhancer, anti-adhesion agent, germicide, analgesic, antiseptic, or pharmaceutically acceptable salts, esters, or prodrugs thereof. In particular embodiments, the therapeutic agent is selected from the group consisting of rapamycin, marcaine, Cyclosporine A (referred to herein as "CSA"), ISA 247 (referred to herein as "ISA") and rifampicin.

In another aspect, provided herein is a method of forming therapeutic fatty acid particles comprising: (a) combining a cross-linked, fatty acid-derived biomaterial (e.g., a cross-linked fish oil) and a therapeutic agent to form a first composition; (b) submerging, surrounding, or suspending the composition in a cryogenic liquid (c) fragmenting the composition; and (d) optionally removing the dispersing media. In one embodiment, the dispersing media comprises a solvent that will not dissolve the therapeutic agent or the cross-linked, fatty acid-derived biomaterial. In still another embodiment, the solvent is hexane, Isopar, water, ethanol, methanol, Proglyme, methylene chloride, acetonitrile, acetone, MEK, liquid nitrogen, and other solvents that do not fully dissolve the therapeutic agent. In another embodiment, the cross-linked, fatty acid-derived biomaterial is in the form of a film. In another embodiment, the film is coarsely ground prior to association with the therapeutic agent.

In one embodiment, the mean particle size of the particles produced by the methods described herein is in the range of about 1 micron to about 50 microns, e.g., 1 micron to about 10 microns. In another embodiment, the particles have a distribution of size of about 1-20 μm (v,0.1), 21-40 μm (v,0.5), and 41-150 μm (v,0.9).

In another aspect, the invention provides a medical device, comprising: a medical device structure, and a coating formed on at least a portion of the medical device structure, wherein the coating comprises fatty acid particles of the invention. The medical device structure can be a vascular graft, hernia mesh, thin film, or stent.

In another aspect, provided herein are therapeutic fatty acid particles comprising a fatty acid. In one embodiment, the therapeutic fatty acid particles comprise a fatty acid and a therapeutic agent. The source of the fatty acid can be a fish oil. The particles can be further combined with a fish oil to form a therapeutic composition.

In still another aspect, the invention provides a method of making a film comprising exerting pressure on the fatty acid particles such that a film is formed. Thus, provided herein is a therapeutic film comprising pressed therapeutic particles, wherein the therapeutic particles comprise a fatty acid and optionally a therapeutic agent. The film can have enhanced mechanical properties. The particles used to form the film can also comprise a therapeutic agent. As discussed herein, the film can be used for a number of therapeutic applications. The particles can be pressed into a film using, e.g., a Carver Press.

In still another aspect, the invention provides a method of making three-dimensional articles comprising exerting pressure on the fatty acid particles such that a three dimensional article is formed. Thus, provided herein is a three-dimensional article comprising pressed therapeutic particles, wherein the therapeutic particles comprise a fatty acid and optionally a therapeutic agent. The three-dimensional article can be formed from the particles by any applicable method known in the art, including, but not limited to, molding, casting, or extruding.

BRIEF DESCRIPTION OF THE DRAWINGS

The foregoing and other aspects, embodiments, objects, features and advantages of the invention can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the invention.

DETAILED DESCRIPTION

Figure 1:
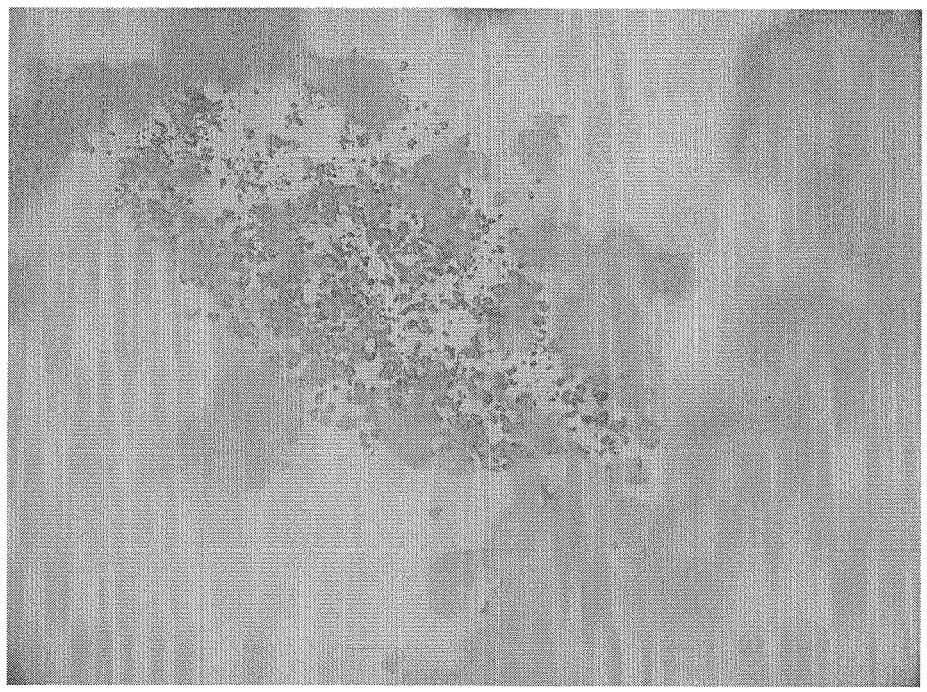
FIG. 1 is a 20× magnified photograph of fatty-acid particles produced using the methods described herein.

As discussed below, the particles described herein are biocompatible, meaning they are compatible with living tissue (e.g., they are not toxic, injurious, or physiologically reactive), and they hydrolyze into non-inflammatory components that are subsequently bio-absorbed by surrounding tissue. As such, the cross-linked, fatty acid-derived materials used to form the particles are referred to as "biomaterials."

In one embodiment, the cross-linked, fatty acid-derived biomaterials are non-polymeric. In another embodiment, the cross-linked, fatty acid-derived biomaterial is a gel, e.g., a gel formed from fish oil.

Cross-linked, fatty acid-derived biomaterials in particle form can be advantageous over other forms of material (such as films) due to the increased surface area of the particles. A cross-linked, fatty acid-derived biomaterial in particle form that is physiologically acceptable, bioabsorbable, and does not induce an inflammatory response can have a significant advantage in drug delivery over current delivery methods. In addition, the cross-linked fatty acid derived particle can be very useful in the delivery of therapeutic agents, e.g., water-insoluble therapeutic agents. As discussed below, fatty-acid based particles can also be used without the addition of therapeutic agents for applications such as adhesion minimization in vivo.

Cross-linked, fatty acid-derived biomaterials in particle form loaded with a therapeutic agent can be used independently to deliver the therapeutic agent in a controlled manner. In addition, the therapeutic loaded fatty acid-derived particles can be used in conjunction with other medical devices (e.g., vascular grafts, hernia mesh, thin films, stents, etc.). These fatty acid-based particles (with or without a therapeutic agent) can also be loaded into fatty acid-based liquids (e.g., fish oil) or gels (e.g., partially cured fish oil) to create an emulsion or suspension.

In various aspects, embodiments can provide methods for forming particles from cross-linked, fatty acid-derived biomaterials. In various embodiments the composition comprises a cross-linked, fatty acid-derived biomaterial (e.g., a cross-linked fish oil), a therapeutic agent, or a combination thereof. The method comprises associating the composition with a cryogenic liquid, and fragmenting the composition into a plurality of particles of desired size using a variety of methods, and removing the cryogenic liquid. In various embodiments, a therapeutic agent is loaded into the cross-linked, fatty acid-derived biomaterial. The therapeutic agent can be added before the composition is fragmented, while the composition is being fragmented, or after the composition has been fragmented.

Suitable fragmentation methods include, but are not limited to, grinding, shearing, shocking, shattering, granulating, pulverizing, shredding, crushing, homogenizing, sonicating, vibrating, and/or milling. Suitable means for fragmenting the cross-linked, fatty acid-derived biomaterial into solid particles include, but are not limited to, mills, e.g., screening mills and impact mills such as hammer mills, and homogenizers, e.g., rotor-stator homogenizers.

Cryogenic Materials for Particle Formation

In various aspects, embodiments can provide methods of producing fatty acid particles. The particles may comprise a cross-linked, fatty acid-derived biomaterial, and optionally a therapeutic agent. Using the methods described herein, cross-linked, fatty acid-derived biomaterials in the form of particles of various particle size can be produced.

As used herein, the term "particle," "particle form," or "fatty acid-based particle" includes solid, partially solid, and gel-like droplets and microcapsules that incorporate a solid, partially solid, gel-like or liquid cross-linked, fatty acid-derived biomaterial, e.g., a cross-linked fish oil. Particles provided and employed herein may have a nominal diameter as large as 999 nanometers, e.g., about 1 micron to about 50 microns.

As used herein, the term "particle size" refers to a number median diameter or a volume median diameter as determined by conventional particle size measuring techniques known to those skilled in the art such as, for example, laser diffraction, photon correlation spectroscopy, sedimentation field flow fractionation, disk centrifugation, electrical sensing zone method, or size classification such as sieving. "Particle size" can also refer to the minimum dimension of a population of particles. For example, particles that are size classified by sieving can have a minimum dimension that is no greater than the size of the holes contained in the sieve.

In various embodiments, the methods described herein may yield particles having a mean particle diameter of 1 micron to about 50 microns, more specifically 1 to 10 microns. In certain embodiments, the methods can yield particles having a mean particle diameter of less than about 1 micron, e.g., 500-999 nanometers. The size of the resulting particles is dependent on the processing conditions and individual characteristics of the composition being processed.

In various embodiments, the method can include the step of fragmenting a composition, e.g., a cross-linked, fatty acid-derived biomaterial, a therapeutic agent, or a combination thereof, while associated with a cryogenic fluid, e.g., liquid nitrogen, thereby forming the particles of desired size. As used herein the term "cryogenic fluid" or "cryogenic liquid" refers to liquefied gases that are maintained in their liquid state at very low temperatures. Exemplary cryogenic fluids include, but are not limited to, liquid nitrogen, liquid helium, liquid neon, and liquid argon. In various embodiments, the cryogenic liquid used is liquid nitrogen. Alternate cryogens are listed in the table below:

| Gas | Normal ° C. |
|---|---|
| Helium-3 | −269.9 |
| Helium-4 | −268.9 |
| Hydrogen | −252.7 |
| Deuterium | −249.5 |
| Tritium | −248.0 |
| Neon | −245.9 |
| Nitrogen | −195.8 |
| Carbon Monoxide | −192.0 |
| Fluorine | −187.0 |
| Argon | −185.7 |
| Oxygen | −183.0 |
| Methane | −161.4 |
| Krypton | −151.8 |
| Tetrafluromethane | −128.0 |
| Ozone | −111.9 |
| Xenon | −109.1 |
| Ethylene | −103.8 |
| Boron trifluoride | −100.3 |
| Nitrous Oxide | −89.5 |
| Ethane | −88.3 |
| Hydrogen chloride | −85.0 |
| Acetylene | −84.0 |
| Fluoroform | −84.0 |
| 1,1-Difluoroethylene | −83.0 |
| Chlorotrifluoromethane | −81.4 |
| Carbon Dioxide | −78.5 (sublimes) |

The compositions can be associated with a cryogenic liquid in a variety of ways, including, but not limited to, being suspended, submerged, surrounded, or cooled by a cryogenic liquid. In various embodiments, the composition is directly associated with the cryogenic liquid, i.e., the composition itself is in contact with the cryogenic fluid. For example, the composition can be suspended in the cryogenic liquid, e.g., liquid nitrogen. The composition can also be indirectly associated with the cryogenic liquid, i.e., the composition is not in contact with cryogenic liquid. For example, the composition can be contained in a vial, and the vial is then suspended, submerged, surrounded, or cooled by a cryogenic liquid.

In various embodiments, the cryogenic liquid is substantially removed after the fragmentation step. One of ordinary skill in the art will recognize methods by which to substantially remove the cryogenic liquid from the composition. For example, the cryogenic liquid, e.g., liquid nitrogen, can be removed by vacuum evaporation to increase the rate of evaporation.

Thus, in one embodiment, provided herein is a method of preparing a fatty-acid derived particle comprising heating a fatty acid-containing material (e.g., a fish oil) to form a cross-linked, fatty acid-derived biomaterial. The resulting material is then contacted with a cryogenic material (e.g., liquid nitrogen), and then fragmented into particle form.

In another embodiment, the cross-linked, fatty acid-derived biomaterial can be first cured to form a film. The resulting film is then contacted with a cryogenic material (e.g., liquid nitrogen), and then fragmented into particle form. Alternatively, the film can be ground to particle form in the absence of a cryogenic liquid. A therapeutic agent can be associated with the particles, either by combing the agent with the fatty acid-containing material before or after heating, combining the agent with the film, and/or combining the agent with the resulting particles. In a non-limiting example, the agent can be dissolved in a solvent (e.g., methanol or ethanol), and sprayed onto or soaked with the material of interest.

As used herein, the term "suspension" or "suspended" refers to a mixture of two substances, one of which is finely divided and dispersed in the other. For example, in various embodiments the composition, e.g., a therapeutic agent alone, a cross-linked, fatty acid-derived biomaterial, or a combination thereof, is dispersed in the cryogenic liquid, e.g., liquid nitrogen.

The term "emulsion," as used herein, includes classic oil-in-water or water in oil dispersions or droplets, as well as other lipid structures that can form as a result of hydrophobic forces that drive polar residues (i.e., long hydrocarbon chains, such as those found in fatty acids) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Such systems possess a finite stability, generally defined by the application or relevant reference system, which may be enhanced by the addition of amphiphilic molecules or viscosity enhancers. Accordingly, the fatty acid-based particles provided herein (with or without a therapeutic agent) also can be loaded into fatty acid based liquids (e.g., fish oil) or gels (e.g., partially cured fish oil) to create an emulsion.

As used herein, the term "dispersing media" refers to any substance capable of dispersing one or more substances within it, without dissolving the dispersed substance. Examples of dispersing media include, but are not limited to, hexane, Isopar, water, ethanol, methanol, nMP, Proglyme, methylene chloride, acetonitrile, acetone, MEK, and liquid nitrogen.

Suitable fragmentation methods include, but are not limited to, grinding, shearing, shocking, shattering, granulating, pulverizing, shredding, crushing, homogenizing, sonicating, vibrating, and/or milling. Suitable means for fragmenting the solid particles include, but are not limited to, mills, e.g., screening mills and impact mills such as hammer mills, and homogenizers, e.g., rotor-stator homogenizers. An example of a suitable mill for fragmenting the material to form particles is the Silverson L4R Homogenizer (Silverson Machines, Inc., East Longmeadow, Mass.). In various embodiments, the starting materials are fragmented into particles by grinding the materials with a mortar and pestle while the materials are suspended in liquid nitrogen.

In various embodiments, the starting materials are fragmented into solid particles by impacting the starting materials with a rod that is magnetically actuated. For example, a Spex Certiprep Cryomill (model 6750) can be used to fragment solid materials into particles. The composition can be placed in an enclosed vial, and a rod like impactor is enclosed in the vial. The vial is maintained at cryogenic temperatures, and the rod is rapidly oscillated in the vial by means of magnets.

The extent to which particle size is formed from the starting materials is dependent on the selected processing parameters, such as the length and number of cycles and the speed of the impactor (impacts/second). For example, if a Spex Certiprep Cryomill is used to fragment the starting materials into particles, the size of the vial the composition is contained in, the amount of composition fragmented, and the size of the impactor will affect the resulting particle size.

In various aspects, a composition comprising a cross-linked, fatty acid-derived biomaterial (e.g., a cross-linked fish oil) is fragmented, thereby resulting in formation of the particles. The cross-linked, fatty acid-derived biomaterial, e.g., the non-polymeric cross-linked fish oil, is bio-absorbable. As utilized herein, the term "bio-absorbable" generally refers to having the property or characteristic of being able to penetrate a tissue of a patient's body. In certain embodiments, bio-absorption occurs through a lipophilic mechanism. The bio-absorbable substance can be soluble in the phospholipid bi-layer of cells of body tissue. It should be noted that a bio-absorbable substance is different from a biodegradable substance. Biodegradable is generally defined as capable of being decomposed by biological agents, or capable of being broken down by microorganisms or biological processes. Biodegradable substances can cause inflammatory response due to either the parent substance or those formed during breakdown, and they may or may not be absorbed by tissues.

Cross-Linked, Fatty Acid-Derived Biomaterial

In various embodiments, the cross-linked, fatty acid-derived biomaterial can be derived from fatty acid compounds. The fatty acids include omega-3 fatty acids when the oil utilized to form the cross-linked, fatty acid-derived biomaterial is fish oil or an analog or derivative thereof. Although some curing methods can have detrimental effects on a therapeutic agent combined with an omega-3 fatty acid oil starting material, one characteristic that can remain after certain curing by, e.g., heating and UV irradiation methods, is the non-inflammatory response of tissue when exposed to the cured omega-3 fatty acid material. As such, an oil containing omega-3 fatty acids can be heated, UV irradiated, or both for curing purposes, and still maintain some or even a majority of the therapeutic effectiveness of the omega-3 fatty acids. In addition, although the therapeutic agent combined with the omega-3 fatty acid and cured with the omega-3 fatty acid can be rendered partially ineffective, the portion remaining of the therapeutic agent can maintain pharmacological activity and in some cases be more effective than an equivalent quantity of agent delivered with other coating materials.

As liquid fish oil is heated, autoxidation occurs with the absorption of oxygen into the fish oil to create hydroperoxides in an amount dependent upon the amount of unsaturated (C=C) sites in the fish oil. However, the (C=C) bonds are not consumed in the initial reaction. Concurrent with the formation of hydroperoxides is the isomerization of (C=C) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C—C) bridges. The formation of the cross-links results in gelation of the fish oil. The heating can also result in the isomerization of cis (C=C) bonds into the trans configuration. The (C=C) bonds can also form C—C cross-linking bridges in the glyceride hydrocarbon chains using a Diels-Alder Reaction. In addition to solidifying the material (e.g., a fish oil fatty acid) through cross-linking, both the hydroperoxide and (C=C) bonds can undergo secondary reactions converting them into lower molecular weight secondary oxidation byproducts including aldehydes, ketones, alcohols, fatty acids, esters, lactones, ethers, and hydrocarbons.

UV initiated curing (photo-oxygenation) involves the interaction between a double bond and singlet oxygen produced from ordinary triplet oxygen by light and typically in the presence of a sensitizer such as chlorophyll or methylene blue and results in the formation of hydroperoxides. The chemical reaction is described in the following graphic.

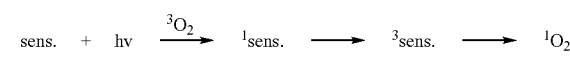

Because the above described reaction is not a radical chain process, the reaction possesses no induction period and is typically unaffected by antioxidants commonly used to inhibit autoxidation. However, this reaction can be inhibited by single oxygen quenchers such as carotene. This reaction is limited to C=C carbon atoms and results in a conversion from cis to trans C=C isomers during curing (as occurs with heat initiated curing). However, photo-oxygenation using UV is a relatively quicker reaction than autoxidation from heat curing, in the realm of about 1000-1500 times faster. The quicker reaction especially holds true for methylene interrupted polyunsaturated fatty acids, such as EPA and DHA, which are found in the fish oil based embodiments.

An important aspect of UV curing when compared to heat curing is that although the byproducts obtained by both curing methods are similar, they are not necessarily identical in amount or chemical structure. One reason for this is due to the ability of photo-oxygenation to create hydroperoxides at more possible C=C sites as shown for linolenate in the below graphic.

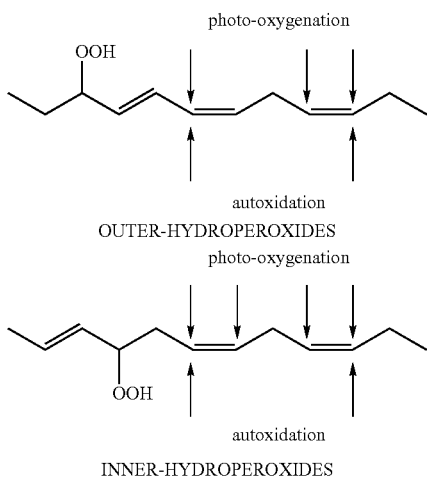

Photo-oxygenation, such as that which results from UV curing, due to its enhanced ability to create inner hydroperoxides, also results in the ability to form relatively greater amounts of cyclic byproducts, which also relates to peroxide cross-linking between fish oil hydrocarbon chains. For example, photo-oxygenation of linolenate results in 6 different types of hydroperoxides to be formed where autoxidation results in only 4. The greater amount of hydroperoxides created using photo-oxygenation results in a similar, but slightly different, structure and amount of secondary byproducts to be formed relative to autoxidation from heat curing. Specifically, these byproducts are aldehydes, ketones, alcohols, fatty acids, esters, lactones, ethers, and hydrocarbons.

Accordingly, in various embodiments, the cross-linked, fatty acid-derived biomaterial that comprises the fatty acid-based particles can be derived from fatty acid compounds, such as those of fish oil, that include a cross-linked structure of triglyceride and fatty acid molecules in addition to free and bound glycerol, monoglyceride, diglyceride, and triglyceride, fatty acid, anhydride, lactone, aliphatic peroxide, aldehyde, and ketone molecules. Without being bound by theory, it is believed that there are a substantial amount of ester bonds remaining (i.e., "partially cross-linked, non-polymeric") after curing in addition to peroxide linkages forming the majority of the cross-links in the material. The cross-linked, fatty acid-derived biomaterial degrades (e.g., by hydrolysis) into fatty acid, short and long chain alcohol, and glyceride molecules, which are all substantially non-inflammatory and likewise can be consumable by cells, such as, e.g., smooth muscle cells. Thus, the cross-linked, fatty acid-derived biomaterial is bio-absorbable and degrades into substantially non-inflammatory compounds.

The bio-absorbable nature of the gel component of the cross-linked, fatty acid-derived biomaterial that comprises the fatty acid-based particles can result in the cross-linked, fatty acid-derived biomaterial being absorbed over time by the cells of the body tissue such that substantially none remains. In various embodiments, there are substantially no substances in the cross-linked, fatty acid-derived biomaterial, or breakdown products, that induce an inflammatory response. For example, in various embodiments, the cross-linked, fatty acid-derived biomaterial upon break-down does not produce either lactic acid or glycolic acid break-down products in measurable amounts. The preferred cross-linked, fatty acid-derived biomaterial is generally composed of, or derived from, omega-3 fatty acids bound to triglycerides, potentially also including a mixture of free fatty acids and vitamin E (alpha-tocopherol). The triglycerides are broken down by lipases (enzymes) which result in free fatty acids that can then be transported across cell membranes. Subsequently, fatty acid metabolism by the cell occurs to metabolize any substances originating with the material. The bio-absorbable nature of the fatty acid-based particles results in the material being absorbed over time.

An advantage of the cured fish oil is that the curing conditions utilized (i.e., cure time and temperature) can directly influence the amount of cross-linking density and byproduct formation, which in turn effects the degradation. Thus, by altering the curing conditions employed, the dissolution rate of a therapeutic compound of interest contained in the cross-linked, fatty acid-derived biomaterial can also be altered.

In various embodiments, an agent, such as, e.g., a free radical scavenger, can be added to the starting material to tailor the drug release profile of the cross-linked, fatty acid-derived biomaterial that comprises the fatty acid-based particles. In various embodiments, antioxidants, e.g., vitamin E, are added to the starting material to, for example, slow down autoxidation in fish oil by reducing hydroperoxide formation, which can result in a decrease in the amount of cross-linking observed in a cured fish oil material. In addition, other agents can be used to increase the solubility of a therapeutic agent in the oil component of the starting material, protect the drug from degradation during the curing process, or both. For example vitamin E can also be used to increase the solubility of certain drugs in a fish oil starting material, and thereby facilitate tailoring the drug load of the eventual cured coating. Thus, varying the amount of Vitamin E present in the coating provides an additional mechanism to alter the cross-linking and chemical composition of the cross-linked, fatty acid-derived biomaterial that comprises the fatty acid-based particles.

In various aspects, the cross-linked, fatty acid-derived biomaterial contains a therapeutic agent. In various embodiments, a therapeutic agent is combined with a fatty acid compound prior to formation of the particle. The resultant particle has the therapeutic agent interspersed throughout the particle.

The cross-linked, fatty acid-derived biomaterial is formed from an oil component. The oil component can be either an oil, or an oil composition. The oil components can comprise one or more of naturally occurring oils, such as fish oil, cod liver oil, cranberry oil, or other oils having desired characteristics. In various embodiments, the oil, e.g., fish oil, is exposed to processing steps, e.g., heating or UV-radiation, to form a cross-linked, fatty acid-derived biomaterial, e.g., a cross-linked fish oil. The material (e.g., fish oil that has fully or partially cross-linked fatty acids) can be further exposed to processing steps, e.g., heating or UV-radiation, to form a film. In various aspects, the film is suspended in liquid nitrogen, and fragmented, thereby forming particles from the film. In various aspects, the film is suspended in liquid nitrogen and fragmented into particles, combined with an oil, e.g., fish oil, and again cryoground into the fish oil thereby producing a substantially thickened formulation.

In various embodiments, a fish oil is used in part because of the high content of omega-3 fatty acids, which can provide, e.g., healing support for damaged tissue, as discussed herein. The fish oil can also serve as an anti-adhesion agent. The fish oil can also maintain anti-inflammatory and/or non-inflammatory properties. The present invention is not limited to formation of the cross-linked, fatty acid-derived biomaterial formulation with fish oil as the naturally occurring oil. However, the following description makes reference to the use of fish oil as one example embodiment. Other oils, such as naturally occurring oils or synthetic oils, can be utilized.

It should be noted that as utilized herein, the term "fatty acid" includes, but is not limited to, omega-3 fatty acid, fish oil, free fatty acid, monoglycerides, di-glycerides, or triglycerides, esters of fatty acids, or a combination thereof. The fish oil fatty acid includes one or more of arachidic acid, gadoleic acid, arachidonic acid, eicosapentaenoic acid, docosahexaenoic acid or derivatives, analogs and pharmaceutically acceptable salts, esters, or prodrugs thereof.

As utilized herein, the term "free fatty acid" includes, but is not limited to, one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, methyl and ethyl esters of fatty acids, fatty alcohols, and analogs and pharmaceutically acceptable salts thereof.

With regard to oils, the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. A fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Unsaturated fatty acids are named according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). EPA and DHA both have anti-inflammatory effects and wound healing effects within the human body.

Cyrogenic Fragmentation

The methods provided herein include the step of fragmenting compositions while associated with a cryogenic fluid, e.g., liquid nitrogen, thereby forming particles. The composition is cooled to cryogenic temperature to ensure that the materials are brittle enough to grind into micron and submicron particle sizes. The cryogenic conditions preserve the physical and chemical characteristics of the ground products from thermal damage. Cryogrinding can achieve a more homogeneous particle sizing. In various embodiments, the compositions include, but are not limited to, cross-linked, fatty acid-derived biomaterials (e.g., cross-linked fish oils), and/or combinations of therapeutic agents and cross-linked, fatty acid-derived biomaterials. The compositions can be associated with a cryogenic liquid by being directly or indirectly suspended, submerged, surrounded or cooled by a cryogenic liquid.

Suitable fragmentation methods include, but are not limited to, grinding, shearing, shocking, shattering, granulating, pulverizing, shredding, crushing, homogenizing, and/or milling. Suitable means for fragmenting the starting materials into solid particles include, but are not limited to, mills, e.g., screening mills and impact mills such as hammer mills, and homogenizers, e.g., rotor-stator homogenizers. The compositions can be fragmented for a number of cycles, i.e., fragmenting the compositions for a specified period of time, followed by a specified period of time in which the compositions are allowed to rest. For example the compositions can be fragmented for 1, 2, 3, 4, 5, 6, 7, 8, 9, or 10 cycles. In various embodiments, the compositions are fragmented from 4 to 8 cycles.

Therapeutic Agents

In various aspects, a therapeutic agent is loaded into the cross-linked, fatty acid-derived biomaterial before particle formation. In another aspect, the cross-linked, fatty acid-derived biomaterial is formed into a film, fragmented (with or without a cryogenic liquid), the resulting particles are combined with a therapeutic agent, and the particle/therapeutic agent composition is further fragmented. Accordingly, the therapeutic agent can be loaded at any time, including before particle formation, during particle formation, or after particle formation. To form the particles, the material, with or without a therapeutic agent, is suspended in a cryogenic liquid, e.g., liquid nitrogen, and fragmented. In various embodiments, the composition is fragmented using a mortar and pestle. If the original starting composition did not have a therapeutic agent, therapeutic agent can then be added to the resulting particles. To further adjust the particle size of the therapeutic agent-containing particles, or to create an emulsion or suspension with the particles, a secondary method, such as a cryogrinder can be used.

In various aspects, a therapeutic agent is combined with a fatty acid compound prior to formation of the film. The resultant film has the therapeutic agent interspersed throughout the film. The film can then be fragmented into particles by any of the methods previously mentioned.

In various aspects, a therapeutic agent is applied in the form of a coating on a stand-alone film. A therapeutic agent can be dissolved in an appropriate solvent (e.g., methanol or ethanol). The therapeutic/solvent mixture is applied to the stand-alone film (dipped, sprayed, or brushed onto the film), and the solvent is evaporated leaving the therapeutic agent loaded into the film. The film is then fragmented into particles by any of the methods previously mentioned.

In various aspects, a therapeutic agent can be loaded into the fragmented particles during the fragmenting process. The therapeutic can be added to the cross-linked, fatty acid-derived biomaterial in powder form, with or without a solubilizer, or a non-solvent and fragmented using any of the methods previously mentioned. If a solvent or non-solvent was used, it can be removed, e.g., dried off, or evaporated. The resulting cross-linked, fatty acid-derived biomaterial particles are loaded with the therapeutic agent.

In various aspects, a therapeutic agent is loaded into the cross-linked, fatty acid-derived biomaterial after the material has been fragmented. For example, a cross-linked, fatty acid-derived biomaterial is fragmented, e.g., suspended in liquid nitrogen and ground with a mortar and pestle. The resulting particles of the cross-linked, fatty acid-derived biomaterial are then soaked in a mixture of a therapeutic agent and a solvent. The solvent is then removed, e.g., dried off or evaporated, yielding cross-linked, fatty acid-derived biomaterial particles loaded with a therapeutic agent. If desired, an additional mortar and pestle or cryogrind cycle may be used to break up any clumping.

As utilized herein, the phrase "therapeutic agent(s)" refers to a number of different drugs or agents available, as well as future agents that can be useful. The therapeutic agent component can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, prodrugs, and analogs or derivatives thereof and any additional desired therapeutic agents such as those listed in Table 1 below.

TABLE 1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 —nitric oxide donor derivative of aspirin, SNAP |
| Gases | Nitric oxide, compound solutions |

TABLE 1-continued

| CLASS | EXAMPLES |
| --- | --- |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma-1b, Interluekin-10 |
| Immunosuppressive/Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ethylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

The therapeutic agent can be an active agent as contained in the cross-linked, fatty acid-derived biomaterial. Pharmaceutically acceptable salts, esters, or prodrugs of the therapeutic agent are also suitable for use. In various embodiments, the cross-linked, fatty acid-derived biomaterial itself comprises the therapeutic agent.

In various embodiments, the therapeutic agent comprises an mTOR targeting compound. The term "mTOR targeting compound" refers to any compound which modulates mTOR directly or indirectly. An example of an "mTOR targeting compound" is a compound that binds to FKBP 12 to form, e.g., a complex, which in turn inhibits phosphoinostide (PI)-3 kinase, that is, mTOR. In various embodiments, mTOR targeting compounds inhibit mTOR. Suitable mTOR targeting compounds include, for example, rapamycin and its derivatives, analogs, prodrugs, esters and pharmaceutically acceptable salts thereof.

Calcineurin is a serine/threonine phospho-protein phosphatase and is composed of a catalytic (calcineurin A) subunit and a regulatory (calcineurin B) subunit (about 60 and about 18 kDa, respectively). In mammals, three distinct genes (A-alpha, A-beta, A-gamma) for the catalytic subunit have been characterized, each of which can undergo alternative splicing to yield additional variants. Although mRNA for all three genes appears to be expressed in most tissues, two isoforms (A-alpha and A-beta) are most predominant in brain.

The calcineurin signaling pathway is involved in immune response as well as apoptosis induction by glutamate excitotoxicity in neuronal cells. Low enzymatic levels of calcineurin have been associated with Alzheimer's disease. In the heart or in the brain calcineurin also plays a key role in the stress response after hypoxia or ischemia.

Substances which are able to block the calcineurin signal pathway can be suitable therapeutic agents. Examples of such therapeutic agents include, but are not limited to, FK506, tacrolimus, cyclosporin and include derivatives, analogs, esters, prodrugs, pharmaceutically acceptably salts thereof, and conjugates thereof which have or whose metabolic products have the same mechanism of action. Further examples of cyclosporin include, but are not limited to, naturally occurring and non-natural cyclosporins prepared by total- or semi-synthetic means or by the application of modified culture techniques. The class comprising cyclosporins includes, for example, the naturally occurring Cyclosporins A through Z, as well as various non-natural cyclosporin derivatives, artificial or synthetic cyclosporin derivatives. Artificial or synthetic cyclosporins can include dihydrocyclosporins, derivatized cyclosporins, and cyclosporins in which variant amino acids are incorporated at specific positions within the peptide sequence, for example, dihydro-cyclosporin D.

In various embodiments, the therapeutic agent comprises one or more of a mTOR targeting compound and a calcineurin inhibitor. In various embodiments, the mTOR targeting compound is a rapamycin or a derivative, analog, ester, prodrug, pharmaceutically acceptably salts thereof, or conjugate thereof which has or whose metabolic products have the same mechanism of action. In various embodiments, the calcineurin inhibitor is a compound of Tacrolimus, or a derivative, analog, ester, prodrug, pharmaceutically acceptably salts thereof, or conjugate thereof which has or whose metabolic products have the same mechanism of action or a compound of Cyclosporin or a derivative, analog, ester, prodrug, pharmaceutically acceptably salts thereof, or conjugate thereof which has or whose metabolic products have the same mechanism of action.

In various embodiments, the therapeutic agent comprises an anti-adhesive agent. As used herein, the term "anti-adhesion agent" refers to any compound that prevents adhesions or accretions of body tissues formed in response to injury of various kinds, e.g., surgery, infection, chemotherapy, radiation. Anti-adhesion agents include, but are not limited to, hyaluronic acid, human plasma derived surgical sealants, and agents comprised of hyaluronate and carboxymethylcellulose that are combined with dimethylaminopropyl, ethylcarbodimide, hydrochloride, PLA, and/or PLGA.

In various embodiments, the therapeutic agent comprises an antiproliferative and/or an antineoplastic agent. The term "antiproliferative/antineoplastic agent" as used herein refers to any compound which inhibits or prevents the growth or development of cells, e.g., smooth muscle cells, or malignant cells. Suitable antiproliferative and antineoplastic agents include, but are not limited to, paclitaxel or its derivatives, analogs, esters, prodrugs, and pharmaceutically acceptable salts thereof.

A therapeutically effective amount refers to that amount of a compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective amount refers to that ingredient alone. When applied to a combination, a therapeutically effective amount can refer to combined amounts of the active ingredients that result in the therapeutic effect, whether administered in combination, serially or simultaneously. In various embodiments, where formulations comprise two or more therapeutic agents, such formulations can be described as a therapeutically effective amount of compound A for indication A and a therapeutically effective amount of compound B for indication B, such descriptions refer to amounts of A that have a therapeutic effect for indication A, but not necessarily indication B, and amounts of B that have a therapeutic effect for indication B, but not necessarily indication A.

Actual dosage levels of the active ingredients in the compositions provided herein can be varied so as to obtain an amount of the active ingredients which is effective to achieve the desired therapeutic response without being unacceptably toxic. The selected dosage level will depend upon a variety of pharmacokinetic factors including the activity of the particular therapeutic agent (drug) employed, or the ester, salt or amide thereof, the mechanism of drug action, the time of administration, the drug release profile of the coating, the rate of excretion of the particular compounds being employed, the duration of the treatment, other drugs, compounds and/or materials used in combination with the particular compounds employed, and like factors known in the medical arts.

As used herein, the term "solid therapeutic agent" refers to therapeutic agents in solid form, i.e., not liquids or gases.

In one embodiment, the therapeutic agent is stabilized. The biologically active agent can be stabilized against degradation, loss of potency and/or loss of biological activity, all of which can occur during formation of the particles having the biologically active agent dispersed therein, and/or prior to and during in vivo release of the biologically active agent from the particles. In one embodiment, stabilization can result in a decrease in the solubility of the biologically active agent, the consequence of which is a reduction in the initial release of the biologically active agent, in particular, when release is from particles for sustained release of the biologically active agent. In addition, the period of release of the biologically active agent from the particles can be prolonged.

Stabilization of the biologically active agent can be accomplished, for example, by the use of a stabilizing agent or a specific combination of stabilizing agents. "Stabilizing agent," as that term is used herein, is any agent which binds or interacts in a covalent or non-covalent manner or is included with the biologically active agent.

In another embodiment, the stabilizing agent can be vitamin E. It should be noted that as utilized herein to describe the present invention, the term "vitamin E" and the term "alpha-tocopherol," are intended to refer to the same or substantially similar substance, such that they are interchangeable and the use of one includes an implicit reference to both. Further included in association with the term vitamin E are such variations including but not limited to one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

The therapeutic agents that can be used with the fatty acid-derived particles of the invention can also include antimicrobial agents, including, antivirals, antibiotics, antifungals and antiparasitics. Specific antimicrobial agents that can be used with the the fatty acid-derived particles of the invention of the invention include Gentamicin Sulfate, Penicillin G, ephalothin, Ampicillin, Amoxicillin, Augmentin, Aztreonam, Imipenem, Streptomycin, Gentamicin, Vancomycin, Clindamycin, Erythromycin, Azithromycin, Polymyxin, Bacitracin, Amphotericin, Nystatin, Rifampicin, Tetracycline, Doxycycline, Chloramphenicol, Nalidixic acid, Ciprofloxacin, Sulfanilamide, Gantrisin, Trimethoprim, Isoniazid (INH), para-aminosalicylic acid (PAS), Minocycline, and silver compounds, such as silver nitrate, silver benzoate, and nano-silver.

"Sustained release," as that term is used herein, is a release of the biologically active agent from the fatty acid-based particles that occurs over a period which is longer than the period during which a biologically significant amount of the active agent would be available following direct administration of the active agent, e.g., a solution or suspension of the active agent. In various embodiments, a sustained release is a release of the biologically active agent which occurs over a period of at least about one day such as, for example, at least about 2, 4, 6, 8, 10, 15, 20, 30, 60, or at least about 90 days. A sustained release of the active agent can be a continuous or a discontinuous release, with relatively constant or varying rates of release. The continuity of release and level of release can be affected by the biologically active agent loading, and/or selection of excipients to produce the desired effect.

"Sustained release," as used herein, also encompasses "sustained action" or "sustained effect." "Sustained action" and "sustained effect," as those terms are used herein, refer to an increase in the time period over which the biologically active agent performs its therapeutic, prophylactic and/or diagnostic activity as compared to an appropriate control. "Sustained action" is also known to those experienced in the art as "prolonged action" or "extended action."

Uses of Particles

The fatty acid-based particles, either alone or in combination with an additional therapeutic agent, can be used in vivo in a variety of ways. For example, the particles can be used as a dry powder in inhaler treatments, as an aqueous dispersion for intravenous use, or in a capsule for oral delivery. The particles can also be applied topically. In various embodiments, the particles can be sprinkled over a desired location in vivo. The particles can be used with another medical device, e.g., a graft or mesh. The particles can also be used without another medical device, e.g., as anti-adhesion particles.

The fatty acid particles of the invention can be used for the prevention of surgical adhesion, as they can minimize surgical adhesions without causing inflammation by being placed in a desired location. Thus, for example, the particles can be sprinkled over a desired location in vivo, e.g., an area of a surgical procedure, for purposes of preventing surgical adhesions.

Also provided herein is a fatty acid-based material (in particle form or particles pressed into a film) suitable for treating or preventing disorders related to vascular injury and/or vascular inflammation. The fatty acid-based material (in particle form or particles pressed into a film) can also be used to treat or prevent injury to tissue, e.g., soft tissue. In another embodiment, the source of the fatty acid for the material is an oil, such as fish oil.

In general, four types of soft tissue are present in humans: epithelial tissue, e.g., the skin and the lining of the vessels and many organs; connective tissue, e.g., tendons, ligaments, cartilage, fat, blood vessels, and bone; muscle, e.g., skeletal (striated), cardiac, or smooth; and nervous tissue, e.g., brain, spinal chord and nerves. The fatty acid-based material of the invention (in particle form or particles pressed into a film) can be used to treat injury to these soft tissue areas. Thus, in one embodiment, the fatty acid-based materials of the invention in particle form or particles pressed into a film) can be used for promotion of proliferation of soft tissue for wound healing. Furthermore, following acute trauma, soft tissue can undergo changes and adaptations as a result of healing and the rehabilitative process. Such changes include, by are not limited to, metaplasia, which is conversion of one kind of tissue into a form that is not normal for that tissue; dysplasia, with is the abnormal development of tissue; hyperplasia, which is excessive proliferation of normal cells in the normal tissue arrangement; and atrophy, which is a decrease in the size of tissue due to cell death and resorption or decreased cell proliferation. Accordingly, the fatty acid-based material of the invention (in particle form or particles pressed into a film) can be used for the diminishment or alleviation of at least one symptom associated with or caused by acute trauma in soft tissue.

In one embodiment, as described below, the fatty acid-based material (in particle form or particles pressed into a film) can be used, for example, to prevent tissue adhesion. The tissue adhesion can be a result of blunt dissection. Blunt dissection can be generally described as dissection accomplished by separating tissues along natural cleavage lines without cutting. Blunt dissection is executed using a number of different blunt surgical tools, as is understood by those of ordinary skill in the art. Blunt dissection is often performed in cardiovascular, colo-rectal, urology, gynecology, upper GI, and plastic surgery applications, among others.

After the blunt dissection separates the desired tissues into separate areas, there is often a need to maintain the separation of those tissues. In fact, post surgical adhesions can occur following almost any type of surgery, resulting in serious postoperative complications. The formation of surgical adhesions is a complex inflammatory process in which tissues that normally remain separated in the body come into physical contact with one another and attach to each other as a result of surgical trauma.

It is believed that abdominal adhesions are formed when bleeding and leakage of plasma proteins from damaged tissue deposit in the abdominal cavity and form what is called a fibrinous exudate. Fibrin, which restores injured tissues, is sticky, so the fibrinous exudate may attach to adjacent anatomical structures in the abdomen. Post-traumatic or continuous inflammation exaggerates this process, as fibrin deposition is a uniform host response to local inflammation. This attachment seems to be reversible during the first few days after injury because the fibrinous exudates go through enzymatic degradation caused by the release of fibrinolytic factors, most notably tissue-type plasminogen activator (t-PA). There is constant play between t-PA and plasminogen-activator inhibitors. Surgical trauma usually decreases t-PA activity and increases plasminogen-activator inhibitors. When this happens, the fibrin in the fibrinous exudate is replaced by collagen. Blood vessels begin to form, which leads to the development of an adhesion. Once this has occurred, the adhesion is believed to be irreversible. Therefore, the balance between fibrin deposition and degradation during the first few days post-trauma is critical to the development of adhesions (Holmdahl L. *Lancet* 1999; 353: 1456-57). If normal fibrinolytic activity can be maintained or quickly restored, fibrous deposits are lysed and permanent adhesions can be avoided. Adhesions can appear as thin sheets of tissue or as thick fibrous bands.

Often, the inflammatory response is also triggered by a foreign substance in vivo, such as an implanted medical device. The body sees this implant as a foreign substance, and the inflammatory response is a cellular reaction to wall off the foreign material. This inflammation can lead to adhesion formation to the implanted device; therefore a material that causes little to no inflammatory response is desired.

Thus, the fatty acid-based material (in particle form or particles pressed into a film) can be used as a barrier to keep tissues separated to avoid the formation of adhesions, e.g., surgical adhesions. Application examples for adhesion prevention include abdominal surgeries, spinal repair, orthopedic surgeries, tendon and ligament repairs, gynecological and pelvic surgeries, and nerve repair applications. The fatty acid-based material may be applied over the trauma site (e.g., in the case of particles, in may be sprinkled) or (e.g., in the case of the pressed film) wrapped around the tissue or organ to limit adhesion formation. The addition of therapeutic agents to the fatty acid-based material (in particle form or particles pressed into a film) used in these adhesion prevention applications can be utilized for additional beneficial effects, such as pain relief or infection minimization. Other surgical applications of the fatty acid-based pressed film may include using the film as a dura patch, buttressing material, internal wound care (such as a graft anastomotic site), and internal drug delivery system. The fatty acid-based material (in particle form or particles pressed into a film) may also be used in applications in transdermal, wound healing, and non-surgical fields. The fatty acid-based material (in particle form or particles pressed into a film) may be used in external wound care, such as a treatment for burns or skin ulcers. The fatty acid-based material (in particle form or particles pressed into a film) may be used without any therapeutic agent as a clean, non-permeable, non-adhesive, non-inflammatory, anti-inflammatory dressing, or the fatty acid-based material (in particle form or particles pressed into a film) may be used with one or more therapeutic agents for additional beneficial effects. When used in any of the aforementioned methods, the fatty acid-based material (in particle form or particles pressed into a film) may or may not be associated with a therapeutic agent.

The process of wound healing involves tissue repair in response to injury and it encompasses many different biologic processes, including epithelial growth and differentiation, fibrous tissue production and function, angiogenesis, and inflammation. Accordingly, the fatty acid-based material (in particle form or particles pressed into a film) provides an excellent material suitable for wound healing applications.

Also, the administration of a variety of therapeutic agents using the particles of the invention is advantageous, as the particles have an increased surface area and increased bioavailability over other carrier agents. Furthermore, the particles of the invention will not induce an inflammatory response in vivo.

In various embodiments, the particles formed by the methods provided herein can be mixed with an oil to create an emulsion, or insoluble formulation. The oil can be cured or uncured. Such a formulation can be used as an extended release coating on a medical device, e.g., a graft or a mesh. The formulation can also be spread onto a substrate surface and allowed to cure for a period of time to cure the layer of the formulation, without degrading the drug.

The particles alone or with an additional therapeutic agent can also be sprinkled onto a stand alone film comprised of a cross-linked, fatty acid-derived biomaterial prior to the film being cured, e.g., placed in an oven. The resulting textured film can then be used in vivo.

The fatty acid particles can be cryoground with a fatty acid compound, e.g., a fish oil, which will substantially thicken the fatty acid compound to a gel-like substance. The viscosity is directly related to the ratio of particles to the fatty acid compound, as well as the length of cure of the fatty acid compound mixture.

Modulated Healing

Also provided herein are fatty acid based-particles suitable for achieving modulated healing in a tissue region in need thereof, wherein the composition is administered in an amount sufficient to achieve said modulated healing. In one embodiment, the source of the fatty acid for the particles is an oil, such as fish oil.

Modulated healing can be described as the in-vivo effect observed post-implant (e.g., from sprinkling) in which the biological response is altered resulting in a significant reduction in foreign body response. As utilized herein, the phrase "modulated healing" and variants of this language generally refers to the modulation (e.g., alteration, delay, retardation, reduction, detaining) of a process involving different cascades or sequences of naturally occurring tissue repair in response to localized tissue injury, substantially reducing their inflammatory effect. Modulated healing encompasses many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other. For example, the fatty acids described herein can alter, delay, retard, reduce, and/or detain one or more of the phases associated with healing of vascular injury caused by medical procedures, including, but not limited to, the inflammatory phase (e.g., platelet or fibrin deposition), and the proliferative phase. In one embodiment, "modulated healing" refers to the ability of a fatty acid-based particle to alter a substantial inflammatory phase (e.g., platelet or fibrin deposition) at the beginning of the tissue healing process. As used herein, the phrase "alter a substantial inflammatory phase" refers to the ability of the particle to substantially reduce the inflammatory response at an injury site. In such an instance, a minor amount of inflammation may ensue in response to tissue injury, but this level of inflammation response, e.g., platelet and/or fibrin deposition, is substantially reduced when compared to inflammation that takes place in the absence of the fatty acid-based particle.

In another non-binding example, the modulated healing effect can be attributed to the modulation (e.g., alteration, delay, retardation, reduction, detaining) of signaling between the cells and proteins that compose the vessel wall and various components of the bloodstream that would otherwise initiate the vascular healing process. Stated differently, at the site of vascular injury, the particles can modulate the interaction of cells of the vessel wall, such as endothelial cells and/or smooth muscle cells, with other cells and/or proteins of the blood that would otherwise interact with the damaged cells to initiate the healing process. Additionally, at the site of vascular injury, the particles can modulate the interaction of proteins of the vessel wall with other cells and/or proteins of the blood, thereby modulating the healing process. When used in any of the aforementioned methods, the fatty acid-based material (in particle form or particles pressed into a film) may or may not be associated with a therapeutic agent.

The fatty acid derived material (in particle form or particles pressed into a film) can be designed to maintain its integrity for a desired period of time, and then begin to hydrolyze and be absorbed into the tissue that it is surrounded by. Alternatively, the fatty acid derived material (in particle form or particles pressed into a film) can be designed such that, to some degree, it is absorbed into surrounding tissue immediately after the fatty acid derived material (in particle form or particles pressed into a film) is inserted in the subject. Depending on the formulation of the particles, it can be completely absorbed into surrounding tissue within a time period of 1 day to 24 months, e.g., 1 week to 12 months, e.g., 1 month to 10 months, e.g., 3 months to 6 months.

Medical Devices

Figure 13A:
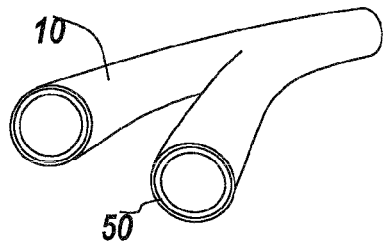
FIGS. 13A-13E are various images of medical devices that can be coated with the particles of the invention.
Figure 13B:
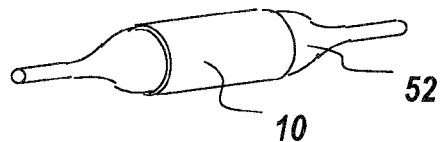
Figure 13C:
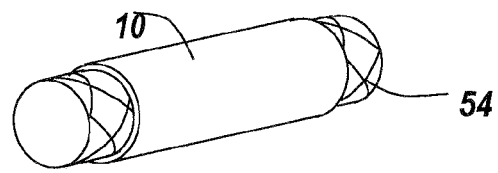
Figure 13D:
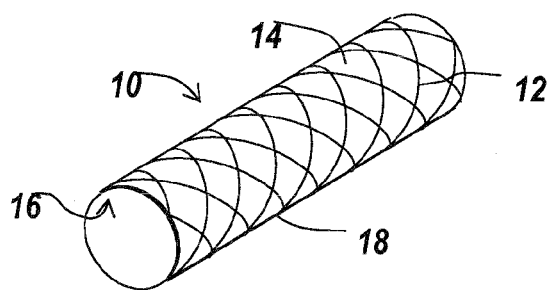
Figure 13E:
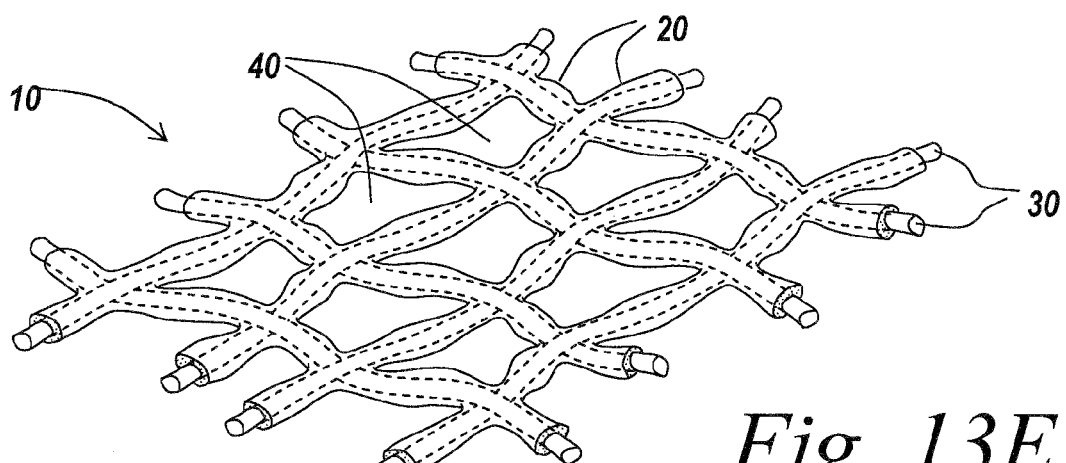

FIGS. 13A-13E illustrate some forms of medical devices mentioned above that can be combined with the particles. In one embodiment, the particles can be used to coat the medical devices. FIG. 13A shows a graft 50 with the particles 10 coupled or adhered thereto. FIG. 13B shows a catheter balloon 52 with the particles 10 coupled or adhered thereto. FIG. 13C shows a stent 54 with the particles 10 coupled or adhered thereto. FIG. 13D illustrates a stent 10 in accordance with one embodiment of the present invention. The stent 10 is representative of a medical device that is suitable for having particles applied thereon to effect a therapeutic result. The stent 10 is formed of a series of interconnected struts 12 having gaps 14 formed therebetween. The stent 10 is generally cylindrically shaped. Accordingly, the stent 10 maintains an interior surface 16 and an exterior surface 18. FIG. 13E illustrates a coated surgical mesh, represented as a biocompatible mesh structure 10, in accordance with one embodiment of the present invention. The biocompatible mesh structure 10 is flexible, to the extent that it can be placed in a flat, curved, or rolled configuration within a patient. The biocompatible mesh structure 10 is implantable, for both short term and long term applications. Depending on the particular formulation of the biocompatible mesh structure 10, the biocompatible mesh structure 10 will be present after implantation for a period of hours to days, or possibly months, or permanently.

Each of the medical devices illustrated, in addition to others not specifically illustrated or discussed, can be combined with the particles of the invention using the methods described herein, or variations thereof. Accordingly, the present invention is not limited to the example embodiments illustrated. Rather the embodiments illustrated are merely example implementations of the present invention.

EXAMPLES

Various aspects and embodiments of the present invention are further described by way of the following Examples. The Examples are offered by way of illustration and not by way of limitation.

1. Fatty Acid-Based Particles Soaked in Rapamycin/Solvent Combination.

A 0.005 inch thin film was made according to the methods described herein. Briefly, fish oil was thickened using heat and oxygen until the desired viscosity was reached. This was accomplished by heating the native fish oil to 93° C. and bubbling oxygen into the heated oil with constant stirring at a rate of 5 standard cubic feet per minute until a viscosity of 20,000 cP @22° C. was reached (a total of 15 hours). The thickened oil was cast onto PTFE coated plates using an adjustable casting knife set at 0.01". The cast oil was UV treated for 15 minutes and then placed into a 200° F. oven for 24 hours to achieve a cross-linked, fatty acid-derived biomaterial film.

The film was then converted into particles either by placing the film into a mortar, covering it with liquid nitrogen and using the pestle to grind it into particle form or by cryogrinding it into particle form. 200 mg each of mortar and pestle film particles and cryoground film particles were soaked in 1 ml of 25 mg/ml rapamycin in ethanol for about 5 minutes. An aluminum weigh pan was lined with 0.45 um filter paper. The particles were poured into the weigh pan and allowed to air dry for about 10 minutes and then placed under vacuum to remove any residual solvent.

Figure 2:
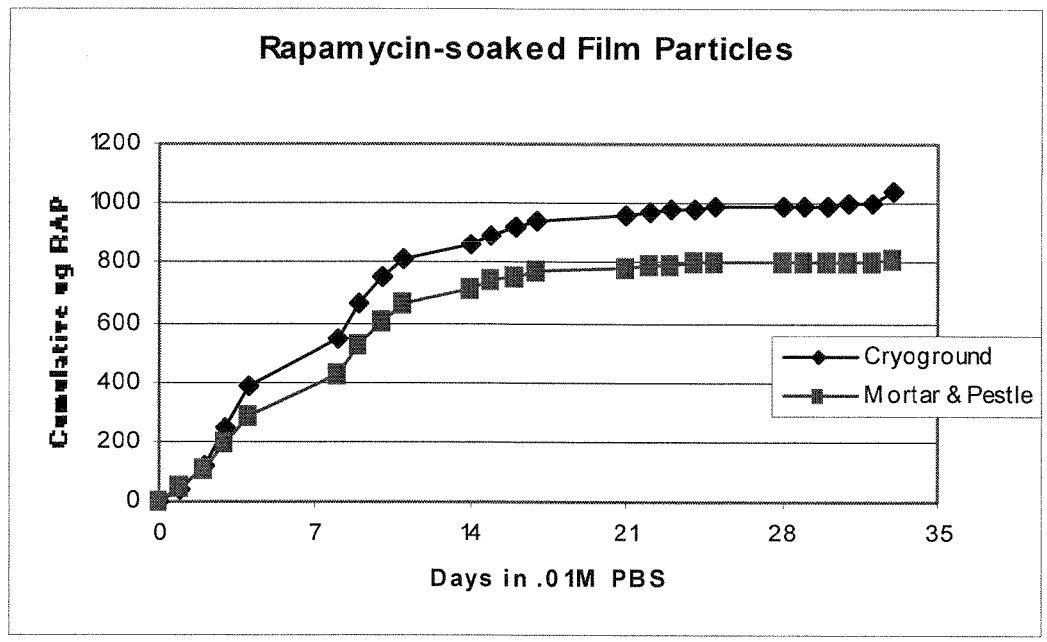
FIG. 2 is a graphical representation of the elution profile of fatty acid-based particles soaked in a rapamycin/solvent combination according to the methods described herein.

40 mg of particles from each grinding method were placed into 3 vials for HPLC analysis: one for dissolution, and two for extraction. Dissolution was conducted in 0.01M PBS. Samples were taken daily. Extraction showed 600 ug RAP per 40 mg of particles using both the mortar and pestle and the cryoground method. The elution profiles are shown in FIG. 2

2. A Thin Film Loaded by Rapamycin/Solvent Spray Prior to Particle Formation

A 0.005" thick non-polymeric cross-linked film was made according to the methods described herein. The film was then cut into two 3×5" film sections. The film sections were sprayed with 25 mg/ml rapamycin/methanol, 4 layers on each side. The films were then ground using a mortar and pestle with liquid nitrogen. 40 mg of particles were then placed into 2 eppendorf tubes for HPLC analysis, one for dissolution and one for extraction. The remaining ground particles were cryoground for eight 2 minute cycles at 30 impacts per second. 40 mg of the cryoground particles were placed into two eppendorf tubes for HPLC analysis, one for dissolution and one for extraction. Extraction showed: 242 ug RAP/40 mg mortar and pestle particles; 229 ug RAP/40 mg cryoground particles.

Figure 3:
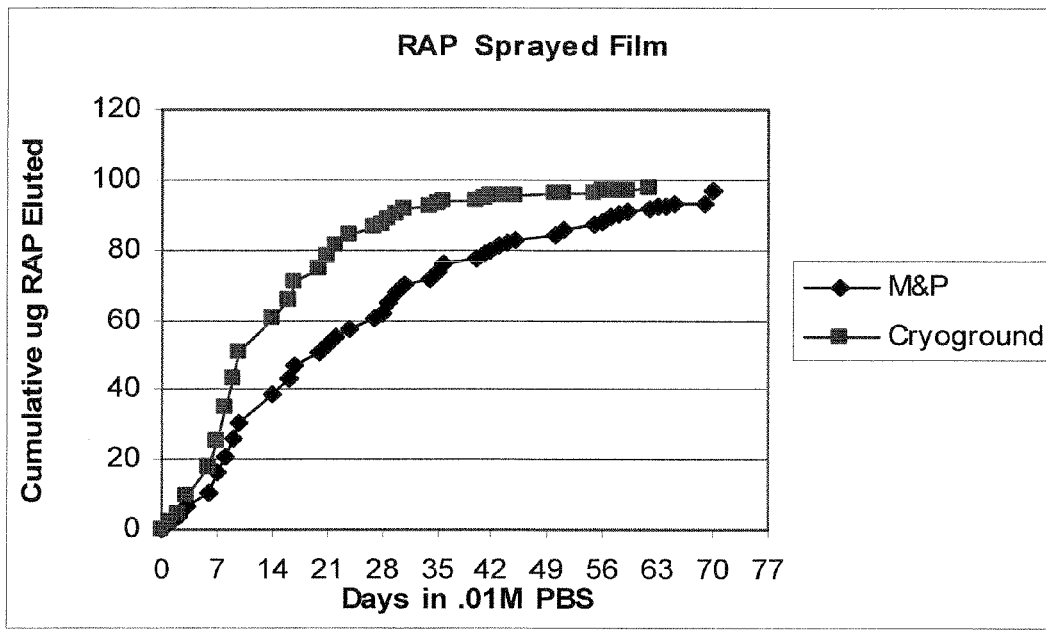
FIG. 3 is a graphical representation of the elution profile of a cross-linked, fatty acid-derived biomaterial film loaded by rapamycin/solvent spray prior to particle formation according to the methods described herein.

Dissolution was conducted in 0.01M PBS. Samples were taken daily. FIG. 3 shows the elution profiles of each group of particles. Both the mortar and pestle particles and the cryoground particles elute similar amounts of RAP by the end of the dissolution, but at different rates.

3. Film Particles Soaked in Cyclosporine A/Solvent

Figure 4:
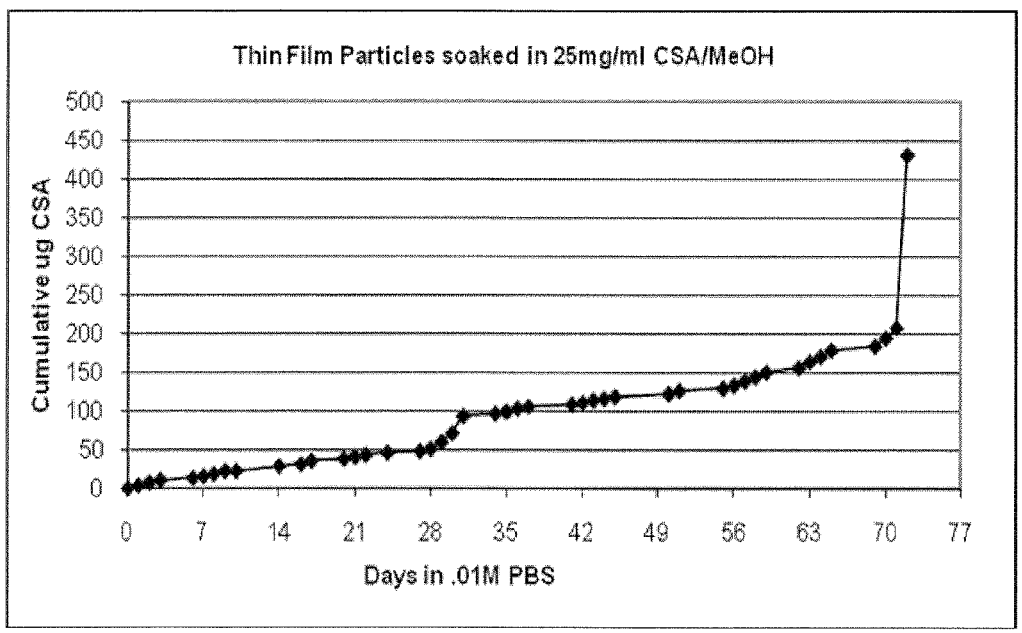
FIG. 4 is a graphical representation of the elution profile of fatty acid-based particles soaked in Cyclosporin A/solvent combination according to the methods described herein.

Two grams of particles derived from cryoground non-polymeric cross-linked film were soaked in 5 ml of 25 mg/ml Cyclosporin A in methanol for approximately 15 minutes. An aluminum weigh pan was lined with 0.45 um filter paper. The particles were poured into the weigh pan and allowed to air dry in the back of the fume hood for 3 hours at ambient conditions. The films were then ground using a mortar and pestle with liquid nitrogen. 40 mg of particles were placed into 4 eppendorf tubes for HPLC analysis, two for dissolution and two for extraction. The particles were extracted using methanol. 40 mg of particles had an average loading of 170 ug of Cyclosporin A. Dissolution was conducted in 0.01M PBS. FIG. 4 shows the elution profile of the particles, the final data point is the final extraction value of CSA from the particles.

Figure 5:
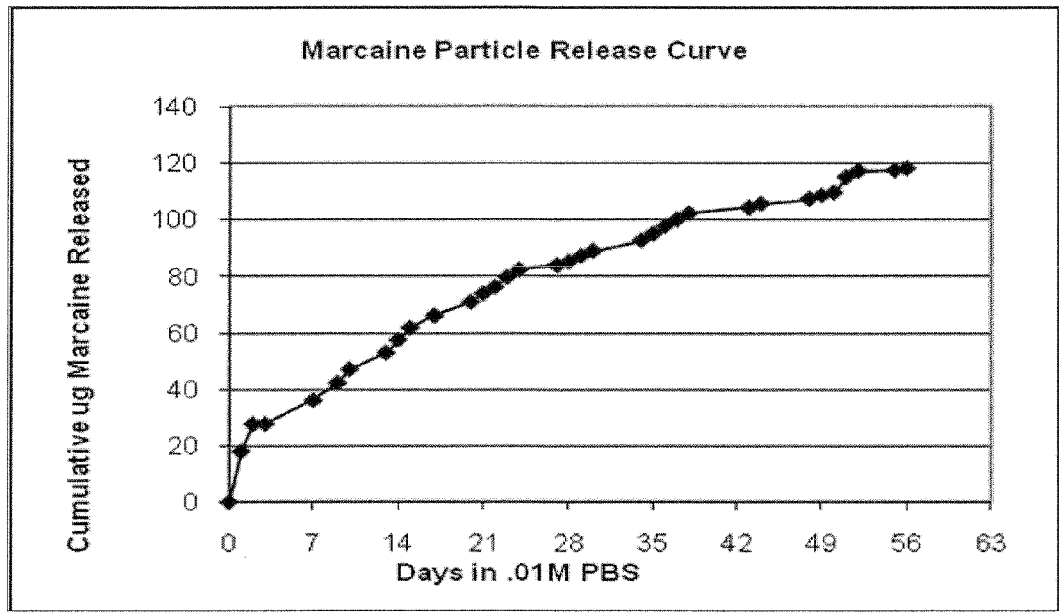
FIG. 5 is a graphical representation of the elution profile of a cross-linked, fatty acid-derived biomaterial film loaded by Marcaine/solvent spray prior to particle formation according to the methods described herein.

4. A Thin Film Loaded by Marcaine/Solvent Spray Prior to being Ground into Particles A thin film comprised of a cross-linked, fatty acid-derived biomaterial, formed from fish oil, approximately 8¼ by 4¾", was sprayed, 3 layers on each side, with 25 mg/ml Marcaine/methanol. The film was then ground using a mortar and pestle with liquid nitrogen. 50 mg of particles were placed into 4 eppendorf tubes for HPLC analysis, two for dissolution and two for extraction. The particles were extracted using acetonitrile. 50 mg of particles had an average loading of 180 ug Marcaine. Dissolution was conducted in 0.01M PBS and samples were taken daily. FIG. 5 shows the elution profile for these particles.

5. Use of Particles Comprising a Cross-Linked, Fatty Acid-Derived Biomaterial for Drug Delivery in a Multi-Lumen Vascular Graft A multi-lumen vascular graft was manufactured using the methods described in U.S. Pat. No. 5,411,550. The multi-lumen graft comprises a primary lumen and at least one secondary lumen separated from the primary lumen by a wall sufficiently permeable to permit a bioactive material disposed into the secondary lumen to diffuse through the wall into the main lumen or through the wall to the advential surface.

A multi-lumen graft with a primary lumen of 6 mm inside diameter and 0.6 mm secondary lumen is selected. Particles of a cross-linked, fatty acid-derived biomaterial, formed from fish oil, were mixed with a solvent, e.g., acetone, to swell the particles. The swelled particles are then loaded into a syringe with a 22 gauge blunt tip needle attached. The needle is placed into one of the secondary lumens, and pressure is then applied to the plunger on the syringe assembly to force the swelled particles through the needle into the secondary lumen until it is substantially completely filled. This process is repeated for three remaining secondary lumens. Once the lumens were filled, the graft is placed into a 200° F. oven for 30 minutes to evaporate the solvent.

6. Film Particles Cryoground with Drug Powder: Directly, with MeOH and with Hexane Fatty acid particles were prepared by grinding a thin film of fish oil (prepared as described in Example 1) using a mortar and pestle with liquid nitrogen. Two grams of the mortar and pestled particles were cryoground in the Spex Certiprep Cryomill (Model 6750) 3 different ways:

1. with 227 mg RAP and 4 ml Hexane (RAP non-solubilizing solvent);
2. with 224 mg RAP and 4 ml MeOH (RAP solubilizing solvent); and
3. with 223 mg RAP (dry).

All formulations were cryoground for eight 2 minute cycles with 2 minute rest between cycles at an impactor speed of 15. Samples containing solvent were dried down using a vacuum chamber over the weekend (for convenience rather than necessity). The samples that were originally ground with solvent were re-cryoground to remove clumping. Approximately 50 mg of sample was each added to 4 eppendorf tubes (total of 12 tubes) for dissolution and extraction. Extraction was performed using 1 ml of an acetonitrile, acetic acid combination. All three methods had and average loading of 4 mg RAP per 50 mg of particles.

Figure 6:
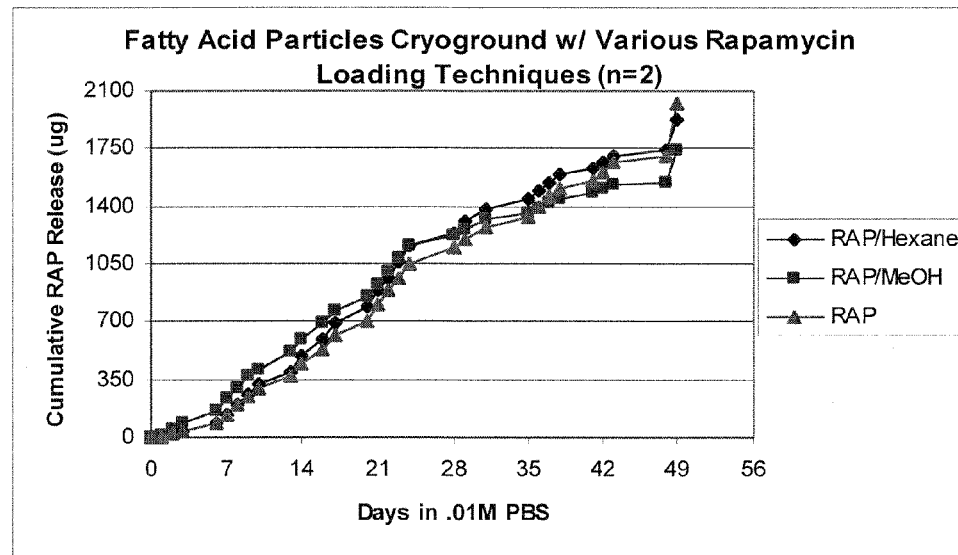
FIG. 6 is a graphical representation of the elution profile of fatty acid-based particles loaded with rapamycin using different methods according to the methods described herein.

Dissolution was conducted in 0.01M PBS and samples were taken daily. FIG. 6 shows the elution profile of the particles (the final data point is the final extraction values of RAP from the particles).

7. Fatty Acid-Based Particles: Cyclosporine Added to the Particle Phase vs. the Oil Phase Fatty acid particles are prepared by grinding a thin film of fish oil (prepared as described herein) using a mortar and pestle with liquid nitrogen, followed by cryogrinding (8 cycles, 2 minute cool, 2 minute cryogrind, 30 impacts/second). 1.2 g cryoparticles are combined with 2.8 g fish oil in a cryovial. The components are then cryoground (8 cycles, 2 minute cool, 2 minute cryogrind, 30 impacts/second). The result is a gel substance.

Optionally, therapeutic agents can be added to the gel either in the particle phase, the oil phase, or both. This example compares the therapeutic loaded into the particle phase vs. the oil phase.

Figure 7:
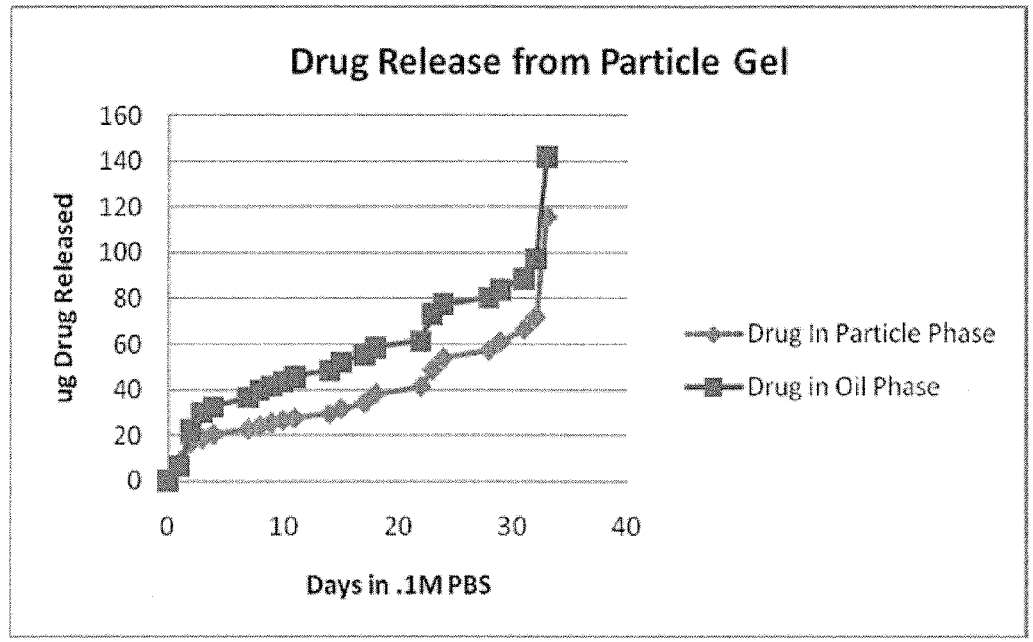
FIG. 7 is a plot showing the average dissolution of two 100 mg samples of the particles described herein in 0.1M PBS.

Particle Phase:
  1.5 g mortar and pestle ground particles
  27.6 mg Cyclosporine A
  Cryogrind these together as described above
  Add: 3.5 g native fish oil
  Cryogrind these together as described above Oil Phase:
  3.5 g native fish oil
  28.5 mg Cyclosporine A
  Heat to solubilize drug
  Add: 1.5 g cryoparticles
  Cryogrind these together as described above The plot shown in FIG. 7 shows the average dissolution of two 100 mg samples in 0.1M PBS. The final data point is the final extraction.

Figure 8:
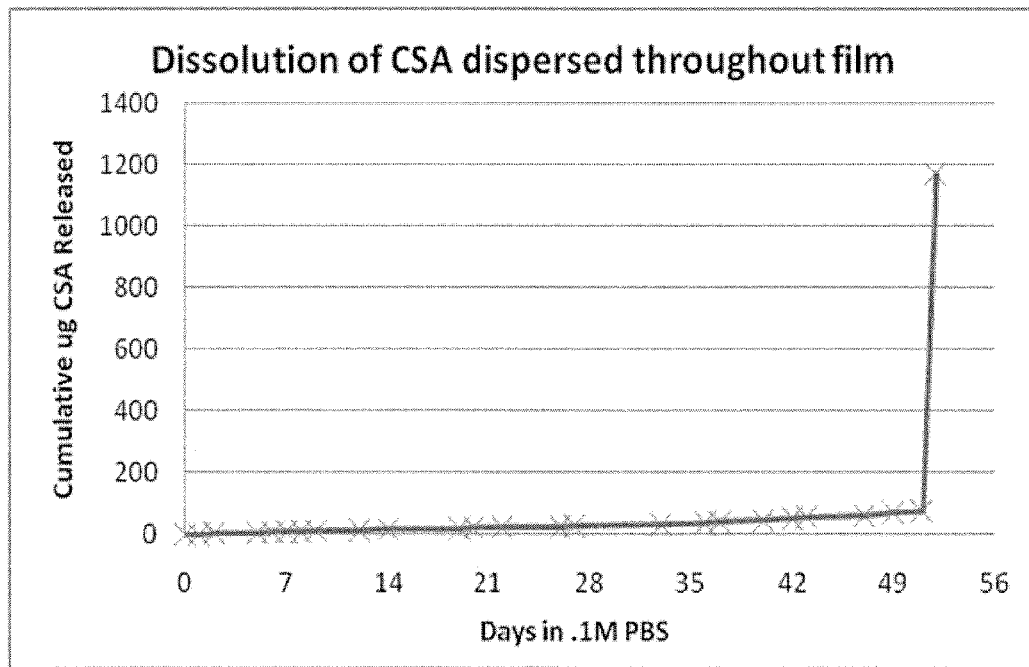
FIG. 8 is a plot demonstrating the average dissolution curve of 1×3" film samples prior to particle formation.

8. CSA Added to Fatty Acid Compound to Form a Thin Film which can be Ground into Fatty Acid Particles Containing CSA Cyclosporine A was directly added to the thickened fish oil at 3.6%, and the resulting composition was solubilized by heating the components at 200° F. for 10 minutes. The oil was then cast into a thin film and cured for 24 hours at 200° F. This film with CSA dispersed within can then be ground into particles. The plot shown in FIG. 8 shows the average dissolution curve of 1×3" film samples prior to particle formation. Each sample contained approximately 1300 ug active CSA (determined by extraction). The last data point is the final extraction. With particle formation it is thought to have more complete release during the dissolution phase due to the increase in surface area.

9. A Pressed Film Comprised of Cured Fish Oil Film Particles Cryoground with Gentamicin Sulfate Fatty acid particles were formed by grinding a cured fish oil film using liquid nitrogen and a mortar and pestle. These particles were then cryoground in the Spex Certiprep Cryomill with 6% Gentamycin Sufate, with a combined particle mass of approximately 3 grams. The formulation was cryoground for eight 2 minute cycles, with 2 minutes of cooling between each cycle, and at a rate of 15 impacts per second. After the particles came to room temperature, they were again ground using liquid nitrogen and a mortar and pestle to separate particles that had clumped together after cryogrinding. The particles were then formed into a thin film using a Carver Press with platen block temperatures of 80° C. and a pressure of 1 ton for 4 minutes. The resulting product was a thin, solid, translucent film.

Figure 9:
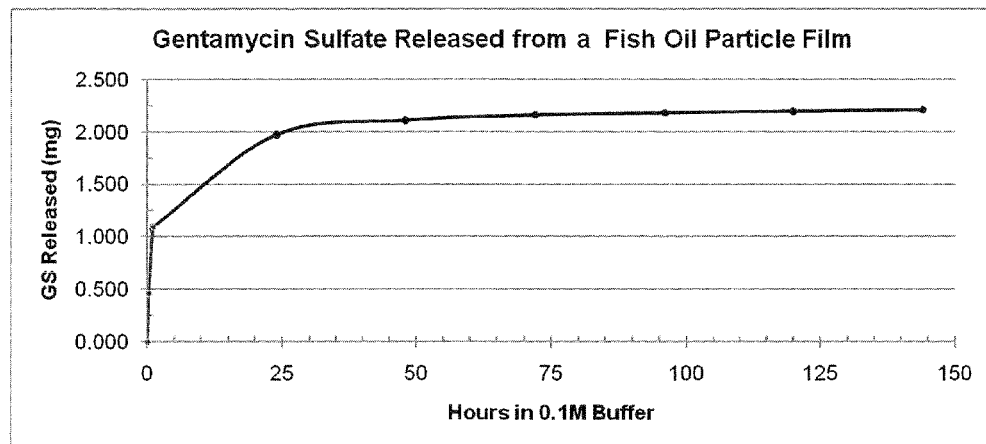
FIG. 9 is a plot demonstrating the average dissolution of Gentamicin Sulfate from a film formed of particles described herein.

FIG. 9 shows the elution profile of the film in 0.1M Phosphate buffer that was carried out for 6 days (144 hours) in a 37° C. shaker table. Although the experiment was stopped at day 6, the therapeutic agent was still releasing at the 6 day timepoint. The total film mass was 197.8 mg with a theoretical gravimetric Gentamicin Sulfate loading of 12 mg. As of 6 days of dissolution, 18.5% of the gravimetric Gentamicin Sulfate had been released.

10. Zone of Inhibition of a Pressed Film Comprised of Cured Fish Oil Film Particles Cryoground with Gentamicin Sulfate In addition to dissolution, an in-vitro zone of inhibition assay was performed on 0.5 inch diameter disks to show efficacy against plates inoculated with *staph aureus*. The zone of inhibition is seen as an antibacterial ring surrounding sample disks where the Gentamicin Sulfate has diffused into the agar. The prepared samples were stored at 37° C. and transferred to a new plate of *staph aureus* daily. The Total Zone Size was measured across the entire diameter of the antibacterial ring, which included the diameter of the sample disk. The data displayed on the bar graph is the difference between Total Zone Size and the Sample Size, resulting in only the size of the actual Zone of Inhibition.

Two sample types were compared with a Zone of Inhibition assay. The first sample type is the pressed particle/Gentamycin Sulfate film that was produced in the same manner as mentioned in the dissolution sample description above. The average gravimetric Gentamicin Sulfate loading of n=3 0.5 inch diameter disks was 480 ug/cm$^2$. The other sample type was made by cryogrinding Gentamicin Sulfate directly with native fish oil and then casting that liquid coating onto bare polypropylene mesh. The sample is exposed to 200° F. for 40 hours to achieve a solid, cured coating. The average gravimetric Gentamicin Sulfate loading of n=2 0.5 inch diameter disks was 406 ug/cm$^2$.

Figure 10:
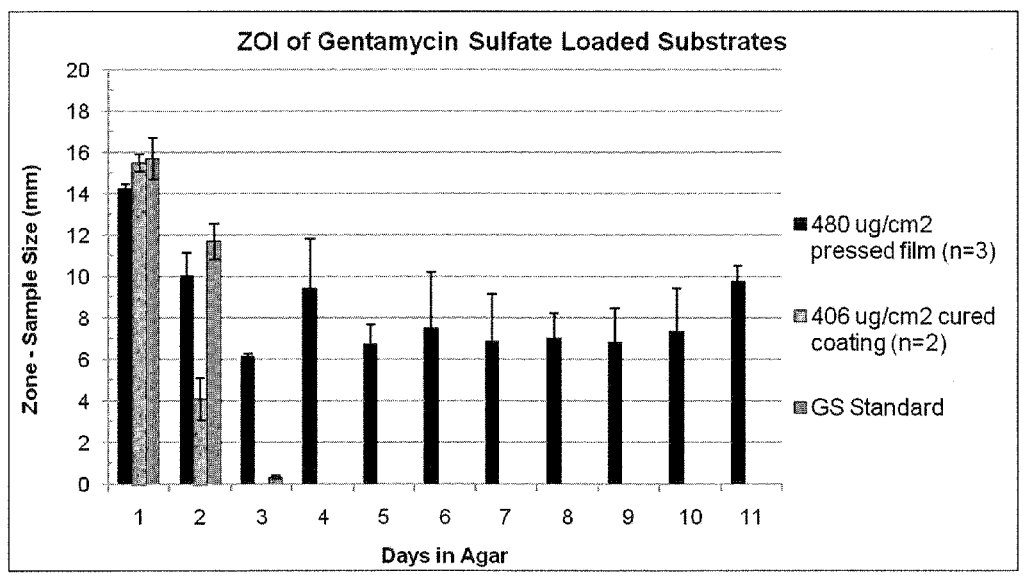
FIG. 10 is a graphical representation of zone of inhibition results from a Gentamicin Sulfate loaded film formed of fatty acid-based particles described herein.

As seen in FIG. 10, the cured mesh samples with Gentamicin Sulfate showed efficacy for two days against *staph aureus*. A 120 ug Gentamycin standard disk was run alongside the cured mesh samples to ensure that the assay was not problematic. In general, these standard disks are efficacious for about 3 days, which was the case for this experiment. The standard shows that the reason the cured mesh samples stopped exhibiting a zone was not a function of the assay, but a function of the samples themselves. In contrast, the pressed particle film with Gentamicin Sulfate has shown activity against *staph aureus* for 11 days in agar. The pressed particle samples are still being carried out in zone of inhibition, and the experiment is not complete at the 11 day time point. Although both sample types were made with comparable amounts of Gentamicin Sulfate, the activity is dependent on how the drug is loaded into the fish oil coating.

11. Film Comprised of Cured Fish Oil Film Particles Cryoground with Gentamicin Sulfate Pressed onto Polypropylene Mesh Fatty acid particles were formed by grinding a cured fish oil film using liquid nitrogen and a mortar and pestle. These particles were then cryoground with 14% Gentamycin Sufate, with a combined particle mass of approximately 3 grams. The formulation was cryoground in the Spex Certiprep Cryomill for eight 2 minute cycles, with 2 minutes of cooling between each cycle, and at a rate of 15 impacts per second. After the particles came to room temperature, they were again ground using liquid nitrogen and a mortar and pestle to separate particles that had clumped together after cryogrinding. The particles were then formed into a thin film using a Carver Press with platen block temperatures of 80° C. and a pressure of 1 ton for 4 minutes. The resulting product was a thin, solid, translucent film. That film was pressed onto one side of a 1"×1" polypropylene mesh using the Carver Press with platen block temperatures of 90° C. and a pressure of 400 lbs for 6 minutes.

Figure 11:
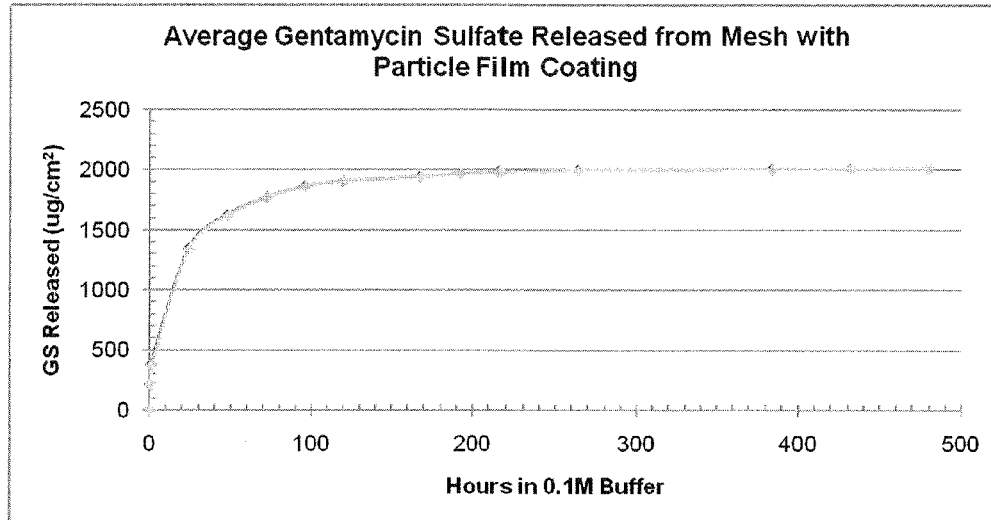
FIG. 11 is a plot demonstrating the average dissolution of Gentamicin Sulfate from a mesh coated with a film formed of fatty acid-based particles described herein.

FIG. 11 shows the elution profile of an average of two mesh-film samples in 0.1M Phosphate buffer that was carried out for 20 days (480 hours) in a 37° C. shaker table. The samples have an average theoretical gravimetric Gentamicin Sulfate loading of 5020 ug/cm². As of 20 days of dissolution, an average of 40.3% of the gravimetric Gentamicin Sulfate has been released.

12. Prevention of Peridural Fibrosis using a Fish Oil Particle in the Rabbit Spinal Model The purpose of this study was to test the efficacy of fish oil particles in the reduction of adhesion formation and biocompatibility at 28 days in a rabbit model of peridural fibrosis.

The particle gel formulation was made by first creating fatty acid particles by cryogrinding a standard 24-hour thin film (as explained in Example 1) using the Spex Certiprep Cryomill, eight two-minute cycles with two-minute cool in between at 30 impacts/second. The particle gel formulation was then prepared by cryogrinding 30% b/w particles in native fish oil using the same cycle parameters.

New Zealand White rabbits were used in the study. A 2-level laminectomy was performed between levels L6 and L4. Using a bur, a 10 mm×5 mm defect was outlined on the lamina of level L5. Drilling was carried out to the level of L4. A similar defect was made on level L6. The dorsal surface of the dura was lightly abraded with a "ball" of 4"×4" sterile gauze (clamped in a pair of hemostats) for a period of 2 minutes to create abrasion trauma on the site of the bone defect.

After conclusion of the surgical procedure the particle gel was placed at the site of the defect to fill the space in the site to receive therapy (randomized to cephalic or caudal in each rabbit). The control site received surgery only.

Twenty eight days post-surgery, the rabbit was euthanized, and the defect was examined based on the appearance of the surrounding tissues, the amount of blood on the surgical site and the amount of bone that regenerated on the surgical site. No differences between control and treated sites were observed for any groups. The vertebra were cut from each end of the defect, treated and sent for histological preparation.

Histologic Evaluation:

Prepared slides were evaluated microscopically. The slides were numbered to blind the evaluator. The sections were evaluated for the effectiveness of the treatment by estimating the amount of epidural fibrosis in histological slides of the healed defect. This was determined by estimating the amount of fibrosis specifically present in the epidural space and fibrosis that was attached to the dura. The amount of fibrosis attached to the dura was determined for each section using the following scoring system:

| | |
|---|---|
| 0 | No fibrosis adherent to dura |
| 1 | 1% to 30% of dura at injury site loosely adhered |
| 2 | 31% to 70% of dura at injury site densely adhered |
| 3 | >70% of dura at injury site densely adhered |

The slides were also evaluated for overall histological appearance (the overall amount of fibrosis including new tissue, the density of the fibrosis, the vascularity of the new tissue filling in the defect site, and the presence or absence of foreign body response) The density of the overall fibrosis and the level of the foreign body reaction were estimated.

The sections were scored using the following system:

| | |
|---|---|
| 0 | No reaction seen |
| 1 | Mild reaction |
| 2 | Moderate reaction |
| 3 | Severe reaction |

Results

Figure 12:
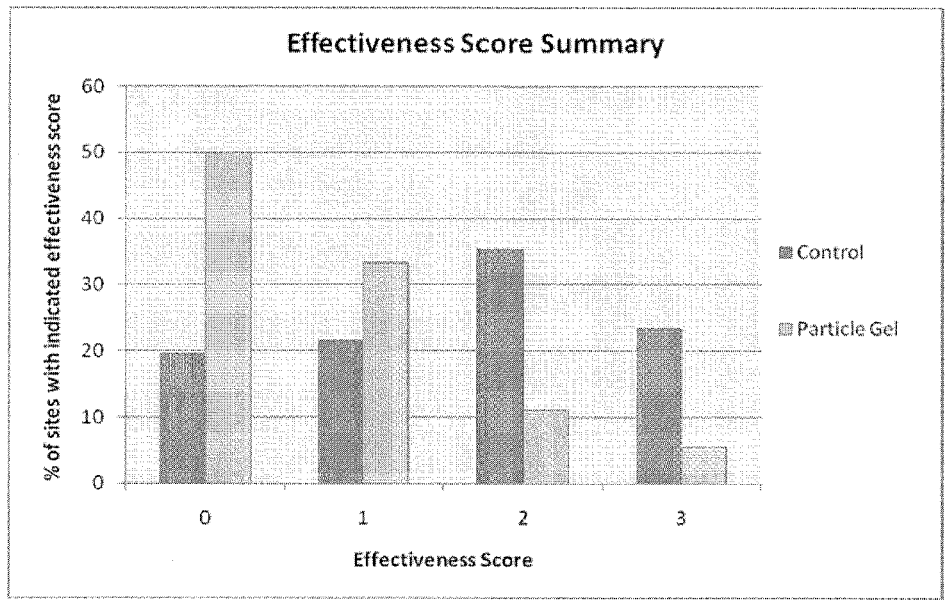
FIG. 12 is a graphical representation of the effectiveness scores from a rabbit peridural fibrosis spine model using a particle material formed with fatty acid-based particles described herein.

As seen in FIG. 12, the particle gel reduced epidural fibrosis (Table 2, p=0.0171). The particle gel samples had large amounts of material detected histologically within the laminectomy site. In the majority of sections (11 of 18), there was no foreign body reaction to the material (Score=0). In the remaining sections, the foreign body reaction was mild (Score=1).

TABLE 2

Effectiveness Scores

| Treatment | Score | Number of Sections with Given Score | Percentage of Sites with Given Score |
|---|---|---|---|
| Control | 0 | 10 | 19.6 |
| | 1 | 11 | 21.6 |
| | 2 | 18 | 35.3 |
| | 3 | 12 | 23.5 |
| Particle Gel | 0 | 9 | 50.0 |
| | 1 | 6 | 33.3 |
| | 2 | 2 | 11.1 |
| | 3 | 1 | 5.6 |

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure can vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail can be made without departing from the scope of the appended claims. Therefore, all embodiments that come within the scope and spirit of the following claims and equivalents thereto are claimed.

The invention claimed is:

1. A method of forming therapeutic fatty acid particles, comprising:
    (a) curing a fish oil combined with a therapeutic agent to form a bioabsorbable material comprising fatty acids cross-linked directly to each other by bonds formed during the curing process, wherein the bioabsorbable material is hydrolyzable by tissue into non-inflammatory components;
    (b) associating the bioabsorbable material with a cryogenic liquid; and
    (c) fragmenting the material/cryogenic liquid composition, such that therapeutic fatty acid particles are formed.

2. The method of claim 1, wherein the material is a cross-linked gel.

3. The method of claim 1, wherein the step of associating the material with a cryogenic liquid comprises at least one of suspending, submerging, and surrounding the material with a cryogenic liquid.

4. The method of claim 1, wherein the cryogenic liquid comprises liquid nitrogen.

5. The method of claim 1, wherein the material/cryogenic liquid composition is fragmented using one or more of grinding, shearing, shocking, shattering, granulating, pulverizing, shredding, crushing, homogenizing, sonicating, vibrating, and/or milling.

6. The method of claim 1, wherein the cryogenic liquid is substantially removed by evaporation, either before fragmentation or after the particles are formed.

7. The method of claim 1, wherein the material is in the form of a film.

8. The method of claim 7, wherein the film is ground prior to association with a cryogenic liquid.

9. The method of claim 1, wherein the mean particle size of the particles is in the range of about 1 micron to about 50 microns.

10. The method of claim 1, wherein the oil further comprises vitamin E.

11. The method of claim 7, wherein the film is coated with a therapeutic agent/solvent mixture.

12. The method of claim 11, wherein the therapeutic agent is dissolved in a solvent, and the therapeutic agent/solvent mixture is applied to the film.

13. The method of claim 12, wherein the therapeutic agent/solvent mixture is applied to the film by dipping or spraying.

14. The method of claim 1, wherein the fatty acid particles are further soaked in a therapeutic agent dissolved in solvent.

15. The method of claims 11 or 14 wherein the solvent is methanol or ethanol.

16. The method of claims 11 or 14 wherein the solvent is hexane, isopar, water, ethanol, methanol, proglyme, methylene chloride, acetonitrile, acetone, or MEK.

17. The method of claim 1, wherein the therapeutic agent comprises one or more of an antioxidant, anti-inflammatory agent, anti-coagulant agent, drug to alter lipid metabolism, anti-proliferative, anti-neoplastic, tissue growth stimulant, functional protein/factor delivery agent, anti-infective agent, imaging agent, anesthetic agent, chemotherapeutic agent, tissue absorption enhancer, anti-adhesion agent, germicide, analgesic, antiseptic, or pharmaceutically acceptable salts, esters, or prodrugs thereof.

18. The method of claim 1, wherein the therapeutic agent is selected from the group consisting of rapamycin, marcaine, CSA, ISA and gentamycin, and rifampicin.

19. A method of forming therapeutic fatty acid particles comprising:
    (a) curing a fish oil to form a bioabsorbable material comprising fatty acids cross-linked directly to each other by bonds formed during the curing process, wherein the bioabsorbable material is hydrolyzable by tissue into non-inflammatory components;
    (b) combining the material and a therapeutic agent to form a composition;
    (c) submerging, surrounding, or suspending the composition in a cryogenic liquid; and
    (d) fragmenting the composition to form therapeutic fatty acid particles comprising cross-linked fatty acids and the therapeutic agent.

20. The method of claim 19, wherein the cryogenic liquid is removed.

21. The method of claim 19, wherein the material is in the form of a film.

22. The method of claim 21, wherein the film is ground into particles before association with the therapeutic agent.

23. A method of forming therapeutic fatty acid particles, comprising the steps of:
    curing a fish oil to form a bioabsorbable material comprising fatty acids cross-linked directly to each other, wherein the bioabsorbable material is hydrolyzable by tissue into non-inflammatory components;
    loading the material with a therapeutic agent before associating the material with a cryogenic liquid; and
    fragmenting the material/cryogenic liquid composition, such that therapeutic fatty acid particles are formed.

24. A method of forming therapeutic fatty acid particles pressed into a film or three dimensional article, the method comprising the steps of:
    curing a fish oil to form a bioabsorbable material comprising fatty acids cross-linked directly to each other, wherein the bioabsorbable material is hydrolyzable by tissue into non-inflammatory components;
    combining the material and a therapeutic agent to form a composition;
    submerging, surrounding, or suspending the composition in a cryogenic liquid;
    fragmenting the composition to form therapeutic fatty acid particles comprising cross-linked fatty acids and the therapeutic agent; and
    pressing the therapeutic fatty acid particles into the film or three dimensional article.

* * * * *